United States Patent
Suresh et al.

(10) Patent No.: US 6,951,555 B1
(45) Date of Patent: Oct. 4, 2005

(54) CATHETER HAVING INTEGRAL EXPANDABLE/COLLAPSIBLE LUMEN

(75) Inventors: Mitta Suresh, Richardson, TX (US); Jill Wright Giannoble, Plano, TX (US); Delos M. Cosgrove, Hunting Valley, OH (US)

(73) Assignee: Chase Medical, L.P., Richardson, TX (US)

( * ) Notice: Subject to any disclaimer, the term of this patent is extended or adjusted under 35 U.S.C. 154(b) by 539 days.

(21) Appl. No.: 09/707,487

(22) Filed: Nov. 7, 2000

Related U.S. Application Data

(63) Continuation-in-part of application No. 09/204,108, filed on Dec. 1, 1998, now Pat. No. 6,179,827.
(60) Provisional application No. 60/078,087, filed on Mar. 16, 1998.

(51) Int. Cl.$^7$ .............................................. A61M 25/00
(52) U.S. Cl. ...................... 604/524; 604/96.01; 604/537
(58) Field of Search ........................... 607/93.01, 96.01, 607/101.01–102.03, 103.01–103.02, 103.05, 103.06, 103.08, 103.09, 523, 533–537, 915, 916, 917, 524–526, 527; 606/191, 192, 194

(56) References Cited

U.S. PATENT DOCUMENTS

| | | | |
|---|---|---|---|
| 2,701,559 A | | 2/1955 | Cooper |
| 2,936,761 A | | 5/1960 | Snyder |
| 3,416,531 A | | 12/1968 | Edwards |
| 3,640,282 A | | 2/1972 | Kamen et al. .............. 128/351 |
| 3,674,033 A | | 7/1972 | Powers |
| 3,802,418 A | | 4/1974 | Clayton |
| 3,884,242 A | | 5/1975 | Bazell et al. ............... 128/351 |
| 3,890,970 A | * | 6/1975 | Gullen ................... 604/170.02 |
| 3,902,492 A | | 9/1975 | Greenhalgh |

(Continued)

FOREIGN PATENT DOCUMENTS

| | | |
|---|---|---|
| DE | 867144 | 2/1953 |
| DE | 3417738 | 11/1985 |
| EP | 150960 | 8/1985 |
| EP | 218275 | 4/1987 |
| EP | 249338 | 12/1987 |
| EP | 266957 | 5/1988 |

(Continued)

OTHER PUBLICATIONS

Sarns Product Brochure, Two Stage Venous Return Catheter Part No. 12340.
Sarns Product Brochure, Wire Reinforced Venous Return Catheter Part No. 14032,36,40.
Sarns Product Brochure, Wire Two Stage Reinforced Venous Return Catheter Part No. 14992.
Medtronic Product brochure, VC2 Atrial–Caval Cannulae.
Medtronic Product Brochure, TAC2 Two Stage, Atrial–Caval Cannulae.

(Continued)

*Primary Examiner*—LoAn H. Thanh
(74) *Attorney, Agent, or Firm*—Meyertons, Hood, Kivlin, Kowert & Goetzel, P.C.; Eric B. Meyertons

(57) ABSTRACT

A catheter and method of use may include an aortic balloon catheter having an integral expandable/collapsible lumen. The catheter comprises a main catheter body having a either a single or a plurality of lumens extending therethrough, and further includes an expandable/collapsible lumen disposed thereabout and carried by the main catheter body. The expandable/collapsible lumen has a relatively large diameter when inflated with respect to the main catheter body, and is self-inflating by fluid pressure when the fluid flows therethrough. The large inflatable/collapsible lumen is attached at its distal end to the main catheter body and thus is carried therewith into a body vessel, and thus is also supported by the catheter body to avoid kinking. The present invention also achieves technical advantages as a catheter for insertion into any body vessel having a limited diameter and which is susceptible to trauma, such as a urethra.

15 Claims, 11 Drawing Sheets

U.S. PATENT DOCUMENTS

| | | |
|---|---|---|
| 3,913,565 A | 10/1975 | Kawahara |
| 3,983,879 A | 10/1976 | Todd .......................... 128/349 |
| 3,995,623 A | 12/1976 | Blake et al. |
| 4,055,187 A | 10/1977 | Patel et al. ................. 128/349 |
| 4,083,369 A | 4/1978 | Sinnreich |
| 4,129,129 A | 12/1978 | Amrine ..................... 128/214 |
| 4,173,981 A | 11/1979 | Mortensen et al. |
| 4,210,478 A | 7/1980 | Shoney |
| 4,211,233 A | 7/1980 | Lin |
| 4,230,119 A | 10/1980 | Blum |
| 4,248,224 A | 2/1981 | Jones |
| 4,249,923 A | 2/1981 | Walda |
| 4,251,305 A | 2/1981 | Becker et al. ................. 156/86 |
| 4,276,874 A | 7/1981 | Wolvek et al. |
| 4,284,073 A | 8/1981 | Krause et al. |
| 4,285,341 A | 8/1981 | Pollack |
| 4,290,428 A | 9/1981 | Durand et al. |
| 4,297,115 A | 10/1981 | Johnson, Jr. |
| 4,301,797 A | 11/1981 | Pollack |
| 4,321,920 A | 3/1982 | Gillig |
| 4,328,056 A | 5/1982 | Snooks ....................... 156/242 |
| 4,351,341 A | 9/1982 | Goldberg et al. |
| 4,375,816 A | 3/1983 | Labianca |
| 4,397,335 A | 8/1983 | Doblar et al. |
| 4,402,684 A | 9/1983 | Jessup |
| 4,406,656 A * | 9/1983 | Hattler et al. ................ 604/523 |
| 4,413,989 A | 11/1983 | Schjeldahl et al. ........... 604/96 |
| 4,416,280 A | 11/1983 | Carpenter et al. |
| 4,417,576 A | 11/1983 | Baran .................... 128/207.15 |
| 4,423,725 A | 1/1984 | Baran et al. ........... 128/207.15 |
| 4,427,009 A | 1/1984 | Wells et al. |
| 4,433,971 A | 2/1984 | Lindsay et al. |
| 4,437,856 A | 3/1984 | Valli |
| 4,447,590 A | 5/1984 | Szycher |
| 4,449,972 A | 5/1984 | Kruger ........................ 604/96 |
| 4,459,977 A | 7/1984 | Pizon et al. |
| 4,465,072 A | 8/1984 | Taheri |
| 4,474,206 A | 10/1984 | Cannon |
| 4,493,697 A | 1/1985 | Krause et al. |
| 4,501,581 A | 2/1985 | Kurtz et al. |
| 4,512,163 A | 4/1985 | Wells et al. |
| 4,512,762 A | 4/1985 | Spears |
| 4,522,195 A | 6/1985 | Schiff |
| 4,527,549 A | 7/1985 | Gabbay |
| 4,529,397 A | 7/1985 | Hennemuth et al. |
| 4,529,400 A | 7/1985 | Scholten |
| 4,531,935 A | 7/1985 | Berryessa |
| 4,531,936 A | 7/1985 | Gordon ........................ 604/49 |
| 4,535,757 A | 8/1985 | Webster, Jr. |
| 4,540,399 A | 9/1985 | Litzie et al. |
| 4,566,480 A | 1/1986 | Parham |
| 4,568,330 A | 2/1986 | Kujawski et al. |
| 4,571,241 A * | 2/1986 | Christopher ................ 604/104 |
| 4,575,371 A | 3/1986 | Nordqvist et al. |
| 4,577,631 A | 3/1986 | Kreamer |
| 4,580,568 A | 4/1986 | Gianturco |
| 4,587,975 A | 5/1986 | Salo et al. |
| 4,592,340 A | 6/1986 | Boyles ....................... 128/1 D |
| 4,596,548 A | 6/1986 | DeVries et al. ................. 604/4 |
| 4,596,552 A | 6/1986 | DeVries ....................... 604/44 |
| 4,601,706 A | 7/1986 | Aillon ........................ 604/122 |
| 4,601,713 A | 7/1986 | Fuqua |
| 4,606,347 A | 8/1986 | Fogarty et al. |
| 4,610,661 A | 9/1986 | Possis et al. |
| 4,610,662 A | 9/1986 | Weikl et al. .................. 604/53 |
| 4,617,019 A | 10/1986 | Fecht et al. |
| 4,639,252 A | 1/1987 | Kelly et al. ................. 604/282 |
| 4,643,712 A | 2/1987 | Kulik et al. |
| 4,648,384 A | 3/1987 | Schmukler .................. 128/1 D |
| 4,655,745 A | 4/1987 | Corbett |
| 4,655,746 A | 4/1987 | Daniels et al. |
| 4,661,095 A | 4/1987 | Taller et al. ................. 604/103 |
| 4,664,125 A | 5/1987 | Pinto |
| 4,668,215 A | 5/1987 | Allgood |
| 4,676,778 A | 6/1987 | Nelson, Jr. ................... 604/45 |
| 4,680,029 A | 7/1987 | Ranford et al. |
| 4,689,041 A | 8/1987 | Corday et al. ................ 604/53 |
| 4,693,243 A | 9/1987 | Buras |
| 4,697,574 A | 10/1987 | Karcher et al. |
| 4,702,252 A | 10/1987 | Brooks et al. ............... 128/344 |
| 4,705,507 A | 11/1987 | Boyles |
| 4,712,551 A | 12/1987 | Rayhanabad |
| 4,714,460 A | 12/1987 | Calderon |
| 4,721,109 A | 1/1988 | Healey |
| 4,723,549 A | 2/1988 | Wholey et al. |
| 4,741,328 A | 5/1988 | Gabbay ...................... 128/1 D |
| 4,753,637 A | 6/1988 | Horneffer |
| 4,762,130 A | 8/1988 | Fogarty et al. |
| 4,781,682 A | 11/1988 | Patel ........................... 604/96 |
| 4,781,703 A * | 11/1988 | Walker et al. ............... 604/264 |
| 4,782,834 A | 11/1988 | Maguire et al. |
| 4,784,638 A | 11/1988 | Ghajar et al. |
| 4,787,388 A | 11/1988 | Hofmann |
| 4,787,882 A | 11/1988 | Claren |
| 4,790,825 A | 12/1988 | Bernstein et al. |
| 4,795,439 A | 1/1989 | Guest |
| 4,795,446 A | 1/1989 | Fecht et al. |
| 4,801,297 A | 1/1989 | Mueller |
| 4,803,984 A | 2/1989 | Narayanan et al. |
| 4,804,358 A | 2/1989 | Karcher et al. |
| 4,804,365 A | 2/1989 | Litzie et al. |
| 4,808,158 A | 2/1989 | Kreuzer et al. |
| 4,808,163 A | 2/1989 | Laub |
| 4,813,935 A | 3/1989 | Haber et al. |
| 4,817,673 A | 4/1989 | Zoghby et al. |
| 4,820,349 A | 4/1989 | Saab |
| 4,850,969 A | 7/1989 | Jackson |
| 4,863,430 A | 9/1989 | Klyce et al. |
| 4,863,441 A | 9/1989 | Lindsay et al. |
| 4,873,978 A | 10/1989 | Ginsburg |
| 4,877,035 A | 10/1989 | Bogen et al. |
| 4,889,137 A | 12/1989 | Kolobow |
| 4,899,787 A | 2/1990 | Ouchi et al. |
| 4,902,272 A | 2/1990 | Milder et al. |
| 4,913,683 A | 4/1990 | Gregory |
| 4,919,133 A | 4/1990 | Chiang |
| 4,921,478 A | 5/1990 | Solano et al. |
| 4,927,412 A | 5/1990 | Menasche .................... 604/96 |
| 4,931,330 A | 6/1990 | Stier et al. |
| 4,943,275 A | 7/1990 | Stricker |
| 4,943,277 A | 7/1990 | Bolling ....................... 604/96 |
| 4,955,895 A | 9/1990 | Sugiyama et al. |
| 4,957,485 A | 9/1990 | Andersson et al. |
| 4,966,585 A | 10/1990 | Gangemi |
| 4,988,515 A | 1/1991 | Buckberg ................... 424/529 |
| 4,990,139 A | 2/1991 | Jang |
| 4,991,578 A | 2/1991 | Cohen |
| 5,011,469 A | 4/1991 | Buckberg et al. ............... 604/4 |
| 5,013,296 A | 5/1991 | Buckberg et al. ............. 604/44 |
| 5,021,044 A | 6/1991 | Sharkawy |
| 5,021,045 A | 6/1991 | Buckberg et al. ............. 604/53 |
| 5,024,668 A | 6/1991 | Peters et al. ................ 606/194 |
| 5,033,998 A | 7/1991 | Corday et al. ................ 600/18 |
| 5,041,084 A | 8/1991 | DeVries et al. ............... 604/43 |
| 5,041,093 A | 8/1991 | Chu |
| 5,053,008 A | 10/1991 | Bajaj |
| 5,059,178 A | 10/1991 | Ya |
| 5,059,204 A | 10/1991 | Lawson et al. |

| | | | | | | |
|---|---|---|---|---|---|---|
| 5,069,661 A | 12/1991 | Trudell | | 5,383,854 A | 1/1995 | Safar et al. .................... 604/98 |
| 5,069,674 A | 12/1991 | Fearnot et al. | | 5,395,330 A | 3/1995 | Marcadis et al. ............. 604/96 |
| 5,074,849 A | 12/1991 | Sachse | | 5,395,331 A | 3/1995 | O'Neill et al. ................ 604/96 |
| 5,084,033 A | 1/1992 | O'Neill et al. | | 5,401,244 A | 3/1995 | Boykin et al. ................ 604/53 |
| 5,090,960 A | 2/1992 | Don Michael ............. 604/101 | | 5,405,338 A | 4/1995 | Kranys |
| 5,112,305 A | 5/1992 | Barath | | 5,407,435 A | 4/1995 | Sachse |
| 5,116,305 A | 5/1992 | Milder et al. | | 5,411,706 A | 5/1995 | Hubbard et al. |
| 5,125,395 A | 6/1992 | Adair | | 5,423,745 A | 6/1995 | Todd et al. .................... 604/53 |
| 5,135,474 A | 8/1992 | Swan et al. ...................... 604/8 | | 5,423,764 A | 6/1995 | Fry |
| 5,135,484 A | 8/1992 | Wright ........................ 604/28 | | 5,425,708 A | 6/1995 | Nasu |
| 5,149,330 A | 9/1992 | Brightbill .................... 604/280 | | 5,433,700 A | 7/1995 | Peters .......................... 604/4 |
| 5,151,087 A | 9/1992 | Jonkman .................... 604/164 | | 5,437,288 A | 8/1995 | Schwartz et al. |
| 5,158,545 A | 10/1992 | Trudell et al. | | 5,437,637 A | 8/1995 | Lieber et al. ................. 604/96 |
| 5,163,906 A | 11/1992 | Ahmadi | | 5,439,444 A | 8/1995 | Andersen et al. ............. 604/96 |
| 5,167,628 A | 12/1992 | Boyles ........................ 604/101 | | 5,441,484 A | 8/1995 | Atkinson et al. ............. 604/96 |
| 5,171,218 A | 12/1992 | Fonger et al. ............... 604/164 | | 5,441,499 A | 8/1995 | Fritzsch |
| 5,171,232 A | 12/1992 | Castillo et al. | | 5,443,446 A | 8/1995 | Shturman ........................ 604/49 |
| 5,173,346 A | 12/1992 | Middleton | | 5,443,448 A | 8/1995 | DeVries ........................ 604/96 |
| 5,176,661 A | 1/1993 | Evard et al. | | 5,448,989 A | 9/1995 | Heckele |
| 5,180,368 A | 1/1993 | Garrison | | 5,449,342 A | 9/1995 | Hirose et al. |
| 5,186,713 A | 2/1993 | Raible | | 5,449,343 A | 9/1995 | Samson et al. ................. 604/96 |
| 5,192,290 A | 3/1993 | Hilal ............................ 606/159 | | 5,451,204 A | 9/1995 | Yoon ............................. 604/1 |
| 5,195,942 A | 3/1993 | Weil et al. | | 5,451,207 A | 9/1995 | Yock .......................... 604/53 |
| 5,195,969 A | 3/1993 | Wang et al. .................... 604/96 | | 5,452,733 A | 9/1995 | Sterman et al. ............. 128/898 |
| 5,196,024 A | 3/1993 | Barath | | 5,453,099 A | 9/1995 | Lee et al. |
| 5,197,952 A | 3/1993 | Marcadis et al. ............. 604/96 | | 5,458,574 A | 10/1995 | Machold et al. ............ 604/101 |
| 5,209,723 A | 5/1993 | Twardowski et al. | | 5,458,575 A | 10/1995 | Wang ........................ 604/101 |
| 5,213,576 A * | 5/1993 | Abiuso et al. ......... 604/103.01 | | 5,460,608 A | 10/1995 | Lodin et al. .................. 604/96 |
| 5,217,466 A | 6/1993 | Hasson | | 5,460,610 A | 10/1995 | Don Michael |
| 5,219,326 A | 6/1993 | Hattler | | 5,462,523 A | 10/1995 | Samson et al. |
| 5,221,258 A | 6/1993 | Shturman .................... 604/96 | | 5,462,530 A * | 10/1995 | Jang ............................. 604/160 |
| 5,226,427 A | 7/1993 | Buckberg et al. | | 5,466,222 A | 11/1995 | Ressemann et al. .......... 604/96 |
| 5,232,444 A | 8/1993 | Just et al. ...................... 604/96 | | 5,466,225 A | 11/1995 | Davis et al. ................. 604/165 |
| 5,254,091 A | 10/1993 | Aliahmad et al. | | 5,470,313 A | 11/1995 | Crocker et al. |
| 5,254,097 A | 10/1993 | Schock et al. | | 5,472,418 A * | 12/1995 | Palestrant .................... 604/43 |
| 5,269,752 A | 12/1993 | Bennett ........................ 604/28 | | 5,477,856 A | 12/1995 | Lundquist |
| 5,275,622 A | 1/1994 | Lazarus et al. | | 5,478,309 A | 12/1995 | Sweezer et al. ................ 604/4 |
| 5,279,562 A | 1/1994 | Sirhan et al. | | 5,484,409 A | 1/1996 | Atkinson et al. |
| 5,279,596 A | 1/1994 | Castaneda et al. .......... 604/282 | | 5,487,730 A | 1/1996 | Marcadis et al. ............. 604/96 |
| 5,281,203 A | 1/1994 | Ressemann | | 5,490,837 A | 2/1996 | Blaeser et al. |
| 5,290,231 A | 3/1994 | Marcadis et al. ............. 604/96 | | 5,499,996 A | 3/1996 | Hill |
| 5,295,994 A | 3/1994 | Bonutti | | 5,501,667 A | 3/1996 | Verduin, Jr. .................. 604/96 |
| 5,300,015 A | 4/1994 | Runge | | 5,505,698 A | 4/1996 | Booth et al. .................. 604/96 |
| 5,300,022 A | 4/1994 | Klapper et al. | | 5,522,819 A | 6/1996 | Graves et al. |
| 5,304,131 A | 4/1994 | Paskar | | 5,533,957 A | 7/1996 | Aldea .......................... 600/16 |
| 5,306,245 A | 4/1994 | Heaven | | 5,533,968 A | 7/1996 | Muni et al. |
| 5,306,249 A | 4/1994 | Don Michael | | 5,536,250 A | 7/1996 | Klein et al. ................. 604/102 |
| 5,308,319 A | 5/1994 | Ide et al. ....................... 600/18 | | 5,540,653 A | 7/1996 | Schock et al. |
| 5,308,320 A | 5/1994 | Safar et al. | | 5,554,119 A | 9/1996 | Harrison et al. |
| 5,308,323 A | 5/1994 | Sogawa et al. ................ 604/95 | | 5,558,644 A | 9/1996 | Boyd et al. .................. 604/96 |
| 5,308,325 A | 5/1994 | Quinn et al. .................. 604/96 | | RE35,352 E | 10/1996 | Peters .......................... 604/4 |
| 5,312,344 A | 5/1994 | Grinfeld et al. ............. 604/101 | | 5,562,606 A | 10/1996 | Huybregts |
| 5,314,418 A | 5/1994 | Takano et al. ............... 604/282 | | 5,569,201 A | 10/1996 | Burns |
| 5,324,253 A | 6/1994 | McRea et al. | | 5,569,219 A | 10/1996 | Hakki et al. |
| 5,324,260 A | 6/1994 | O'Neill et al. ................ 604/96 | | 5,571,089 A | 11/1996 | Crocker ...................... 604/102 |
| 5,330,451 A | 7/1994 | Gabbay | | 5,571,091 A | 11/1996 | Davis et al. ................. 604/165 |
| 5,334,142 A | 8/1994 | Paradis ........................ 604/53 | | 5,571,215 A | 11/1996 | Sterman et al. ................ 623/66 |
| 5,334,146 A | 8/1994 | Ozasa | | 5,573,508 A | 11/1996 | Thornton .................... 604/96 |
| 5,334,169 A | 8/1994 | Brown et al. ................ 604/282 | | 5,575,771 A | 11/1996 | Walinsky .................... 604/96 |
| 5,336,191 A | 8/1994 | Davis et al. ................. 604/165 | | 5,584,803 A | 12/1996 | Stevens et al. ................ 604/4 |
| 5,338,298 A | 8/1994 | McIntyre .................... 604/96 | | 5,593,394 A | 1/1997 | Kanesaka et al. ........... 604/282 |
| 5,342,325 A | 8/1994 | Lun et al. .................... 604/272 | | 5,597,377 A | 1/1997 | Aldea .......................... 600/16 |
| 5,344,399 A | 9/1994 | DeVries ........................ 604/96 | | RE35,459 E | 2/1997 | Jonkman .................... 604/164 |
| 5,354,288 A | 10/1994 | Cosgrove et al. | | 5,599,325 A | 2/1997 | Ju et al. ...................... 604/282 |
| 5,356,388 A | 10/1994 | Sepetka et al. ............. 604/164 | | 5,605,162 A | 2/1997 | Mirzaee et al. .............. 128/772 |
| 5,358,486 A | 10/1994 | Saab | | 5,607,394 A | 3/1997 | Andersen et al. ............ 604/102 |
| 5,358,493 A | 10/1994 | Schweich, Jr. et al. ...... 604/264 | | 5,607,421 A | 3/1997 | Jeevanandam et al. |
| 5,360,403 A * | 11/1994 | Mische .................. 604/101.02 | | 5,609,571 A | 3/1997 | Buckberg et al. ............. 604/4 |
| 5,363,882 A | 11/1994 | Chikama | | 5,611,775 A | 3/1997 | Machold et al. ............. 604/53 |
| 5,364,357 A | 11/1994 | Aase ............................ 604/96 | | 5,616,149 A | 4/1997 | Barath ........................ 606/159 |
| 5,378,230 A | 1/1995 | Mahurkar .................... 604/43 | | 5,618,267 A * | 4/1997 | Palestrant .................... 604/510 |

| | | |
|---|---|---|
| 5,620,418 A | 4/1997 | O'Neill et al. ............... 604/96 |
| 5,624,380 A | 4/1997 | Takayama et al. |
| 5,634,895 A | 6/1997 | Igo et al. .................. 604/21 |
| 5,645,560 A | 7/1997 | Crocker et al. |
| 5,653,696 A | 8/1997 | Shiber |
| 5,658,251 A | 8/1997 | Ressemann et al. ....... 604/102 |
| 5,658,264 A | 8/1997 | Samson |
| 5,658,311 A | 8/1997 | Baden ..................... 606/192 |
| 5,662,607 A | 9/1997 | Booth et al. .............. 604/96 |
| 5,662,620 A | 9/1997 | Lieber et al. ............. 604/280 |
| 5,674,197 A | 10/1997 | van Muiden et al. |
| 5,695,457 A | 12/1997 | St. Goar et al. |
| 5,695,483 A | 12/1997 | Samson |
| 5,695,519 A | 12/1997 | Summers et al. |
| 5,700,253 A | 12/1997 | Parker |
| 5,702,372 A | 12/1997 | Nelson |
| 5,707,389 A | 1/1998 | Louw et al. |
| 5,716,340 A | 2/1998 | Schweich, Jr. et al. ..... 604/101 |
| 5,735,290 A | 4/1998 | Sterman et al. |
| 5,738,649 A * | 4/1998 | Macoviak ................ 604/43 |
| 5,738,652 A | 4/1998 | Boyd et al. |
| 5,755,660 A | 5/1998 | Tyagi |
| 5,755,687 A | 5/1998 | Donlon |
| 5,755,690 A | 5/1998 | Saab |
| 5,766,151 A | 6/1998 | Valley et al. |
| 5,769,828 A | 6/1998 | Jonkman |
| 5,782,811 A | 7/1998 | Samson et al. |
| 5,795,331 A | 8/1998 | Cragg et al. ............... 604/509 |
| 5,795,332 A | 8/1998 | Lucas et al. ............... 604/96 |
| 5,795,341 A | 8/1998 | Samson |
| 5,799,661 A | 9/1998 | Boyd et al. |
| 5,800,375 A | 9/1998 | Sweezer et al. |
| 5,807,384 A | 9/1998 | Mueller |
| 5,810,757 A | 9/1998 | Sweezer, Jr. et al. |
| 5,813,410 A | 9/1998 | Levin |
| 5,836,926 A | 11/1998 | Peterson et al. |
| 5,843,116 A | 12/1998 | Crocker |
| 5,865,721 A | 2/1999 | Andrews et al. |
| 5,873,865 A | 2/1999 | Horzewski et al. |
| 5,873,866 A | 2/1999 | Kondo et al. |
| 5,875,782 A | 3/1999 | Ferrari et al. |
| 5,885,238 A | 3/1999 | Stevens et al. |
| 5,911,734 A | 6/1999 | Tsugita et al. |
| 5,913,842 A | 6/1999 | Boyd et al. |
| 5,928,181 A | 7/1999 | Coleman et al. |
| 5,941,858 A | 8/1999 | Johnson |
| 5,947,125 A | 9/1999 | Benetti |
| 5,947,940 A | 9/1999 | Beisel |
| 5,951,539 A | 9/1999 | Nita et al. |
| 5,957,879 A | 9/1999 | Roberts et al. |
| 5,965,089 A | 10/1999 | Jarvik et al. |
| 5,984,908 A | 11/1999 | Davis et al. |
| 6,010,531 A | 1/2000 | Donlon et al. |
| 6,015,402 A | 1/2000 | Sahota ..................... 604/523 |
| 6,029,671 A | 2/2000 | Stevens et al. |
| 6,045,531 A | 4/2000 | Davis |
| 6,068,608 A | 5/2000 | Davis et al. ................ 604/4 |
| 6,132,397 A | 10/2000 | Davis et al. |
| 6,135,982 A | 10/2000 | Campbell |
| 6,152,911 A | 11/2000 | Giannoble |
| 6,179,827 B1 | 1/2001 | Davis et al. |
| 6,190,311 B1 | 2/2001 | Glines et al. |
| 6,241,699 B1 | 6/2001 | Suresh et al. |
| 6,258,069 B1 | 7/2001 | Carpentier et al. |
| 6,319,244 B2 | 11/2001 | Suresh et al. |
| 6,458,097 B1 * | 10/2002 | Boussignac ............. 604/96.01 |

FOREIGN PATENT DOCUMENTS

| | | |
|---|---|---|
| EP | 280225 | 8/1988 |
| EP | 357338 | 3/1990 |
| EP | 415332 | 3/1991 |
| EP | 417781 | 3/1991 |
| EP | 451996 | 10/1991 |
| EP | 485903 | 5/1992 |
| EP | 582870 | 2/1994 |
| EP | 664104 | 7/1995 |
| EP | 668058 | 8/1995 |
| EP | 704226 | 4/1996 |
| EP | 730879 | 9/1996 |
| EP | 769307 | 4/1997 |
| EP | 791340 | 8/1997 |
| FR | 2567405 | 1/1986 |
| GB | 1547328 | 6/1979 |
| WO | 8704081 | 7/1987 |
| WO | 9108791 | 6/1991 |
| WO | 9217118 | 10/1992 |
| WO | 9220398 | 11/1992 |
| WO | 9418881 | 9/1994 |
| WO | 9511719 | 5/1995 |
| WO | 9517919 | 7/1995 |
| WO | 9528983 | 11/1995 |
| WO | 9532756 | 12/1995 |
| WO | 9617644 | 6/1996 |
| WO | 9630072 | 10/1996 |
| WO | 9640347 | 12/1996 |
| WO | 9717099 | 5/1997 |
| WO | 9717100 | 5/1997 |
| WO | 9732623 | 9/1997 |
| WO | 9848884 | 11/1998 |
| WO | 9904836 | 2/1999 |
| WO | 9904845 | 2/1999 |
| WO | 9904848 | 2/1999 |
| WO | 0032264 | 6/2000 |
| WO | 0054829 | 9/2000 |

OTHER PUBLICATIONS

"Atheroembolism From The Ascending Aorta", The Journal of Thoracic and Cardiovascular Surgery, C. Blauth et al., Jun. 1992, vol. 103, No. 6, pp. 1104–1111.

Charles C. Reed, Diane K. Clark, Chapter 19, "Cannulation", Chapter 23 Myocardial Protection, Cardiopulmonary Perfusion, Texas Medical Press, Inc., Houston, TX, 1975.

Advertising flyer for "Arglye® Lighthouse Tip Vena Caval Catheter", by Sherwood Medical Company, dated 1985.

Research Medical, Inc, "Retroplegia with Textured Balloon".

A sales description of Mayo cannula from the V. Mueller Co. catalog.

USCI Catalog, "Cardiovascular Catheters and Accessories," 1967–1968, p. 41.

ACMI Catalog, Apr. 1972, p. 18, Pelham NY.

Research Medical, Inc., "Dual Drainage Venous Return Cannulae".

Th. Lavergne et al. (PACE, vol. 12, Jan. 1989, Part II, pp. 177–186)—"Transcatheter Radiofrequency Ablation of Atrial Tissue using a Suction Catheter".

Y. Bar–El et al., "Clamping of the atherosclerotic ascending aorta during coronary artery bypass operations, Its cost in strokes," J Thorac Cardiovasc Surg 1992; 104:469–474.

* cited by examiner

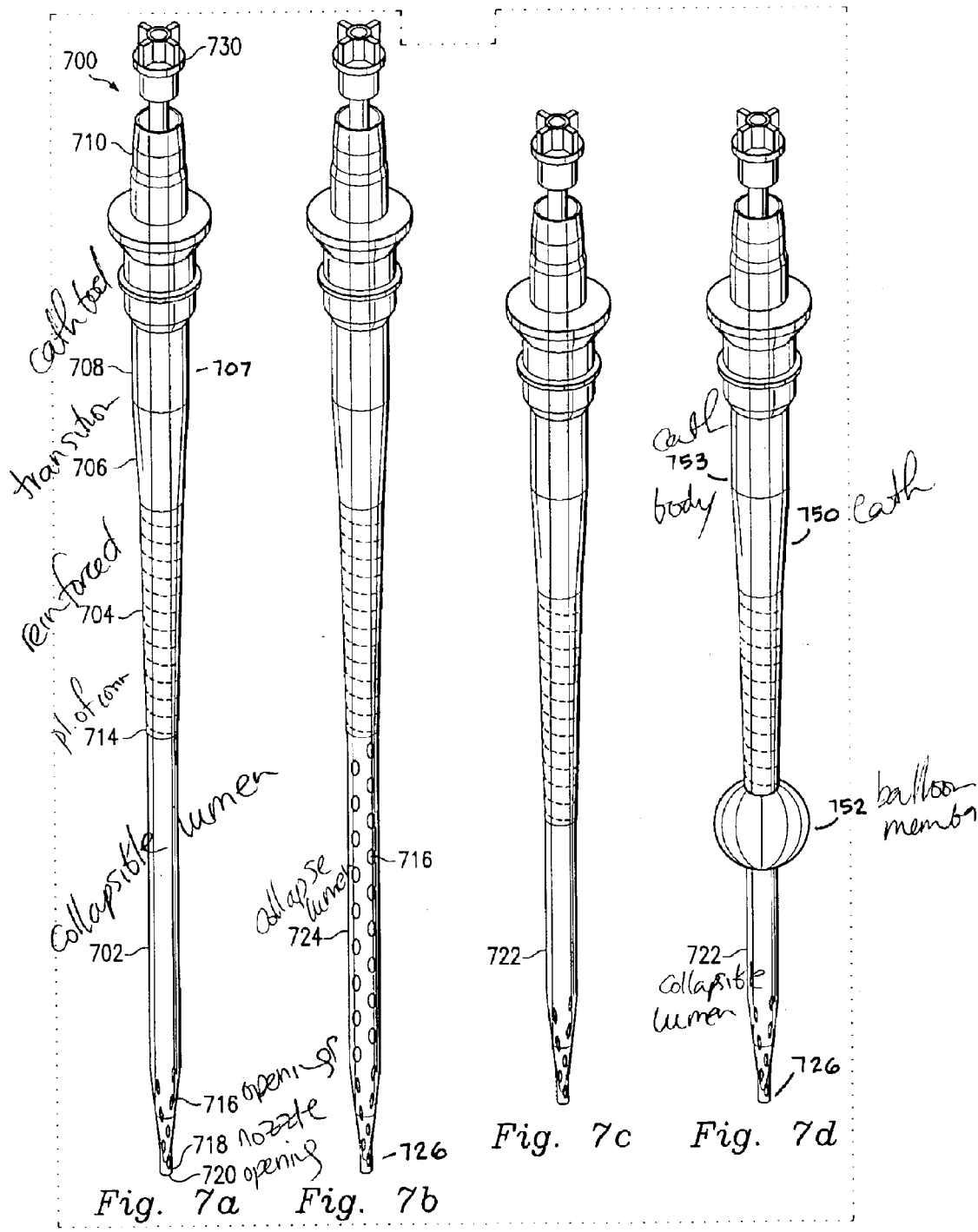

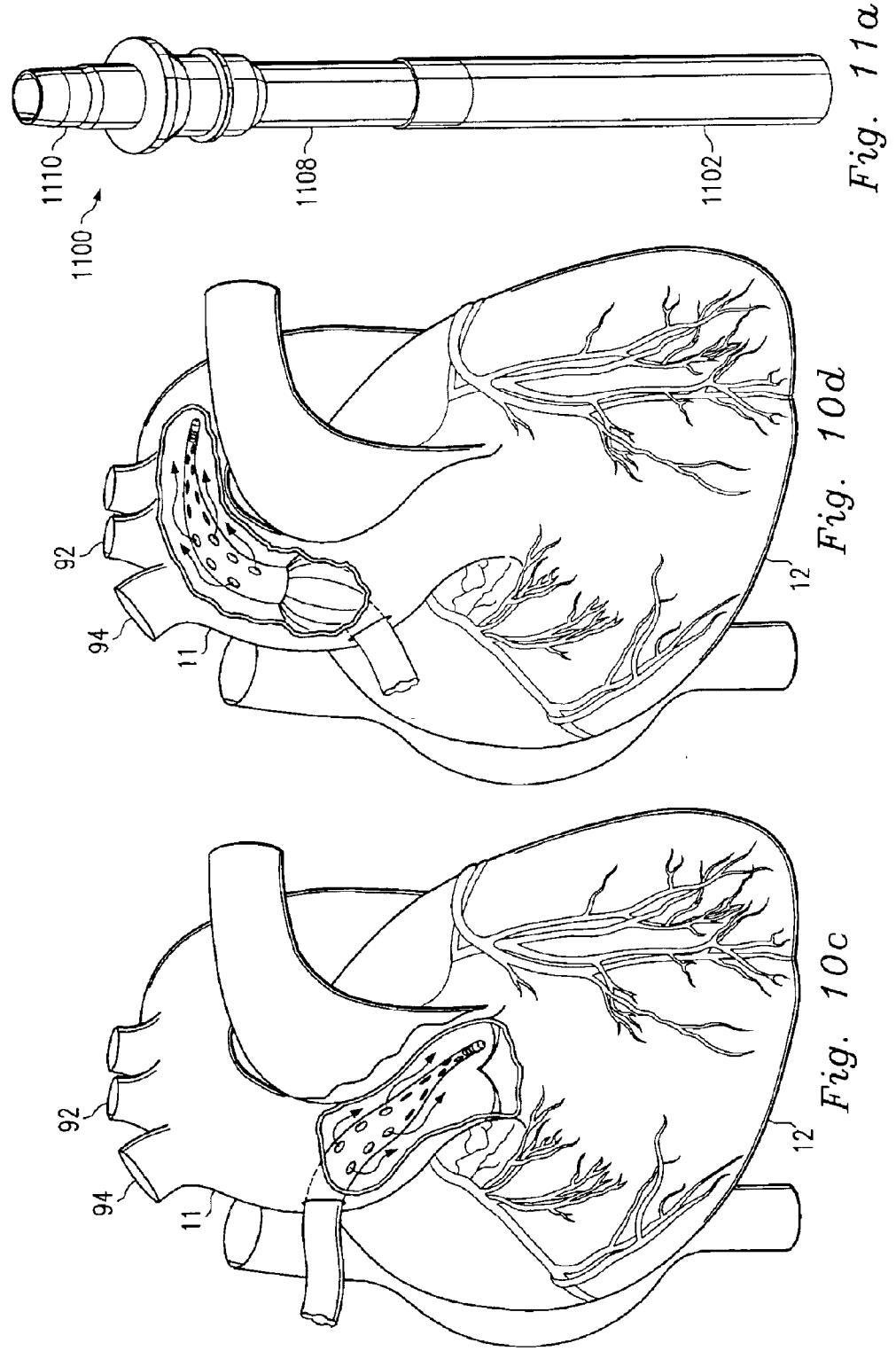

CATHETER HAVING INTEGRAL EXPANDABLE/COLLAPSIBLE LUMEN

CROSS REFERENCE

This application is a continuation in part of application Ser. No. 09/204,108, now U.S. Pat. No. 6,179,827 filed Dec. 1, 1998, which claims the benefit of U.S. Provisional application Ser. No. 60/078,087, filed Mar. 16, 1998.

FIELD OF THE INVENTION

The present invention is generally related to medical catheters and procedures for using the same, and more particularly to catheters adapted to be inserted into body vessels including access vessels having a limited diameter with respect to the cannula diameter.

BACKGROUND OF THE INVENTION

In the medical profession, the use of catheters to deliver and vent fluids from body vessels is becoming more pervasive due to the advancement of minimally invasive procedures. It is often desired to insert a catheter into a body vessel such as the aorta, urethra etc. via an access vessel having a restricted diameter. The catheter usually has a plurality of lumens, for instance, one lumen to infuse a fluid such as a medicant or oxygenated blood, and another lumen for inflating a balloon to selectively occlude the body vessel. The number of lumens, and particularly the aggregate cross sectional area of the lumens, substantially determines the overall catheter diameter. It is desired to keep the overall diameter of the catheter as small as possible, especially with respect to the access vessel and the vessel for which it is intended to be placed to reduce trauma to the vessel.

With respect to aortic balloon catheters in particular, these catheters may be percutaneously inserted into a patient's femoral artery, serving as an access vessel, and advanced upwardly into the aorta of the patient. According to one conventional method, a first catheter is inserted into the femoral artery and advanced into the ascending aorta. The catheter may include a balloon for selectively occluding the aorta and have multiple lumens terminating at the distal end thereof for delivering cardioplegia to the aortic root and/or venting fluid from the aorta above the aortic root. Other lumens may provide for instrumentation to be inserted into the aorta, which may be advanced through the aortic valve into the heart. The proximal end of the catheter may be provided with a lumen terminating proximate the point of insertion to provide arterial return of oxygenated blood. Alternatively, a separate second catheter may be inserted into the patient's other femoral artery to provide arterial return of oxygenated blood. This second catheter is used to reduce the overall diameter of the first catheter body advanced into the aorta, thus reducing trauma to the aorta lining. The distal end of this second catheter is also advanced only to proximate the point of insertion since it is semi-rigid and has a relatively large diameter to provide the required arterial return of oxygenated blood into the aorta. By using a second catheter, a rather large diameter first catheter is not necessary to be inserted into the aorta which may cause trauma to the lining of the artery. However, returning oxygenated blood well below the aorta requires oxygenated blood to flow counter to typical arterial blood flow, upwardly into the ascending aorta to the various arteries branching therefrom.

The disadvantages of this approach include the fact that returning oxygenated blood to the aorta upwardly in a direction counter to normal flow has been found in some studies to be damaging to the artery lining, and which may create aortic dissection, aneurysms, and in some cases death. In addition, this method requires a second infusion catheter to be inserted and manipulated which can be cumbersome.

SUMMARY OF THE INVENTION

The present invention achieves technical advantages as a single catheter having a relatively large inflatable/collapsible lumen suited for insertion via smaller access vessels into larger vessels. The larger lumen is collapsed during insertion, and inflated during fluid delivery. The catheter can be inserted via an access artery and provide arterial return of oxygenated blood into the ascending aorta. This inflatable/collapsible lumen is secured to the main catheter body distal end., and surrounds the main catheter body having multiple lumens for facilitating other functions, such as pressure sensing at the catheter distal end, balloon inflation, and delivery of cardioplegia/venting at the catheter distal end.

In one embodiment, the catheter derives technical advantages as being adapted to be percutaneously positioned into the aorta via a femoral artery with the large lumen in the collapsed position. This large lumen has a very thin wall facilitating inflation/collapsing about the main catheter body, preferably being comprised of polyethylene. Subsequently, by infusing a fluid, such as oxygenated blood, into the large lumen, the large lumen self expands due to fluid pressure of the fluid flowing therethrough to the lumen distal end. In another embodiment, the catheter can be inserted into other access vessels such as a subclavian artery.

The catheter derives technical advantages as a single catheter having multiple lumens and a reduced overall diameter. The catheter has a relatively small overall diameter during insertion through access arteries to the aorta with the large lumen in the collapsed position during advancement. This small diameter provides good control of the catheter during insertion, reducing the risk of damaging or traumatizing the lining of the artery. The catheter main body provides advancement of the large lumen within the vessel, and the catheter is sufficiently rigid to avoid kinking during insertion.

The catheter has other numerous uses and advantages in the surgical field whereby a large catheter lumen is required for exchanging a fluid to a body vessel, but the body vessel has a relatively small diameter and is difficult to navigate in and is susceptible to trauma. For instance, the catheter is ideally suited for use as a ureter catheter as well.

Another embodiment uses a single catheter having a single large cannula with a collapsible lumen attached to the distal end. The cannula body in this embodiment can be any of an number of embodiments having a distal end coupled to collapsible lumen. The catheter may be used for different procedures by varying the length of the collapsible lumen. For instance, if the collapsible lumen is relatively short (approximately 1 inch), the catheter may be used to perfuse blood in the ascending aorta or directly inserted in the distal aortic arch to perfuse blood in the descending aorta On the other hand, if the collapsible lumen is relatively long, the catheter may be inserted from the femoral artery. The collapsible lumen is soft and pliable so that once it is in the blood vessel it is unlikely to cause trauma to the interior lining of the blood vessel. The collapsible lumen may have a larger diameter than the catheter body which allows for a more diffused and gentler flow. The distal end of the collapsible lumen may have a variety of openings.

The collapsible lumen may be folded inside the catheter body or rolled up near the distal end of the catheter. Once the catheter is connected to a heart lung machine, the fluid flow from the machine expands the catheter to its full width and diameter.

In another embodiment, a dilator may be used to insert the collapsible lumen into the artery. The catheter can be inserted in the usual manner, then the collapsible lumen maybe be expanded to the desired length by inserting the dilator through the cannula body and into the expanded section. Alternatively, the collapsible lumen can also be expanded simply by the fluid pressure from a roller pump once the catheter is attached to an extracorporeal circuit.

In yet another embodiment, with the aid of a semi-rigid tube, the collapsible lumen can also be folded inside an insertion cover of a relatively small diameter. After insertion, the cover can simply be peeled off, allowing the collapsible lumen to be expanded by fluid pressure produced by the extracorporeal circuit.

The use of dilator or insertion cover allows insertion and positioning of a thin, flexible cannula without the trauma to the inside of the artery associated with conventional devices. In either case, the flexible lumen can expanded to the full diameter by the pressure of the fluids flowing during perfusion. Furthermore, the use of the diffused nozzles causes a gentler flow during perfusion, which is also significantly reduces the risk of trauma to the aorta.

BRIEF DESCRIPTION OF THE DRAWINGS

FIG. 7a is an isometric side view of one embodiment of the catheter with a tapered distal end;

FIG. 7b is an isometric side view of another embodiment of the catheter with a tapered distal end;

FIG. 7c is an isometric side view of another embodiment of the catheter with a tapered distal end;

FIG. 7d is an isometric side view of another embodiment of the catheter with a tapered distal end;

FIG. 9e is a transverse cross-sectional drawing of the embodiment shown in FIG 9a;

FIG. 10c is a view of the embodiment shown in FIG. 7b inserted into the aorta arch;

FIG. 10d is a view of the embodiment shown in FIG. 7d inserted into the aortic arch and perfusing the descending aorta;

FIG. 11a is an isometric side view of one embodiment showing an expanded lumen;

DESCRIPTION OF THE PREFERRED EMBODIMENT

Figure 1:
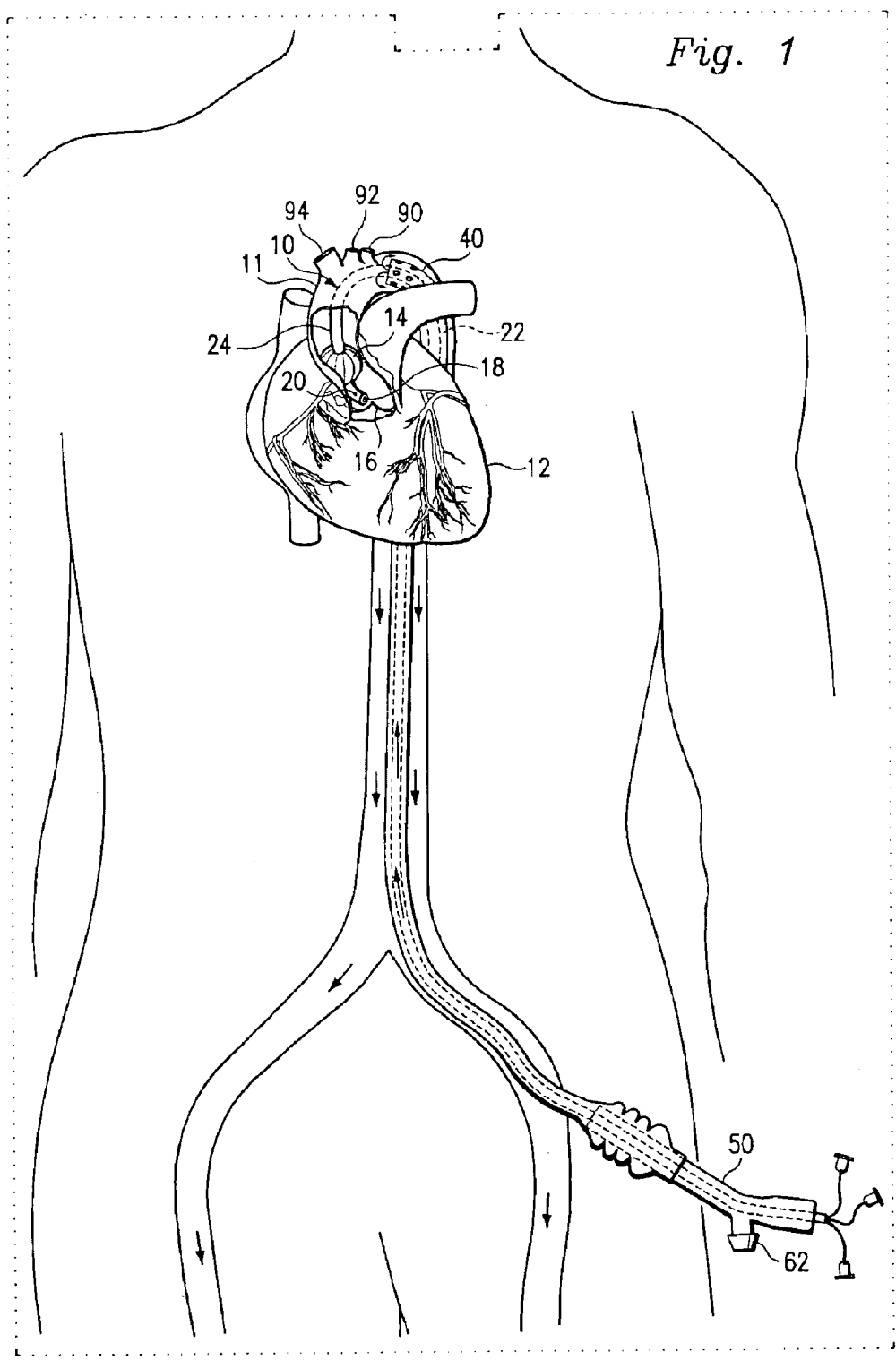
FIG. 1 is a perspective view of the catheter shown femorally inserted into the aorta to provide arterial return of oxygenated blood when the catheter is used as an aortic catheter, wherein the large inflatable lumen is in the collapsed position during insertion to minimize trauma to the arteries and then inflated during delivery of oxygenated blood.

Referring now to FIG. 1, there is shown generally at 10 a catheter according to the preferred embodiment used as an aortic balloon catheter femorally inserted into a patient and advanced into an ascending aorta 11 of a heart 12. Catheter 10 is seen to have a balloon member 14 positioned and expanded within the ascending aorta 11 to occlude the aorta above an aortic valve 16. Catheter 10 is further seen to include a cardioplegia delivery/venting port 18 and a pressure sensing port 20. Both ports 18 and 20 are defined distal of balloon member 14 for use within the ascending aorta above the aortic valve 16. Catheter 10 is further seen to include a large integral expandable/collapsible lumen 22 defined between a main catheter body 24 and a thin-walled sleeve member 40 disposed about and carried by the main catheter body 24. Lumen 22 terminates proximate the distal end of the catheter 10, but proximal the balloon member 14. Lumen 22 is ideal for providing arterial return of oxygenated blood to the ascending aorta from an extracorporeal pump (not shown).

The catheter derives technical advantages as a catheter having a large lumen 22 that can be collapsed when inserted through a smaller access artery, such as the femoral artery, and into the ascending aorta. The catheter has a reduced overall diameter during insertion, thereby reducing trauma to the artery and improving control during insertion. The fluid pressure of the oxygenated blood delivered through lumen 22 causes sleeve member 40 to self expand from a collapsed state within the artery, whereby the diameter of the large lumen 22 is sufficient to provide oxygenated blood at a sufficient rate and pressure to perfuse the human body. As shown, a single catheter 10 is suitable for providing multiple functions during aortic perfusion, without requiring a second catheter and minimizing damage to the lining of the aorta.

Figure 2:
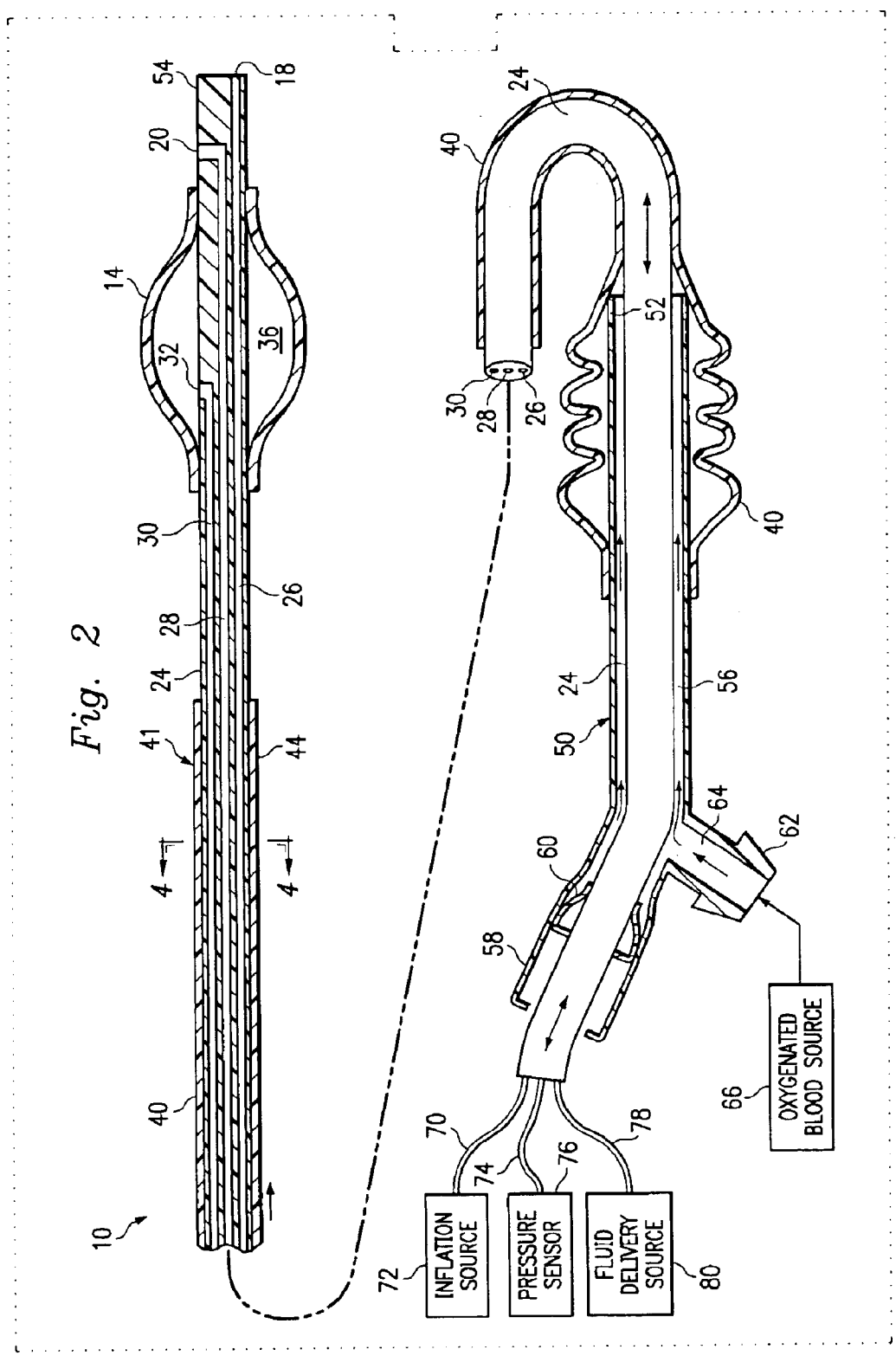
FIG. 2 is a longitudinal cross section of the catheter shown in FIG. 1 including the large inflatable/collapsible lumen shown in the collapsed state as carried by the catheter body for advancement into a body vessel, such as for the procedure shown in FIG. 1.
Figure 3:
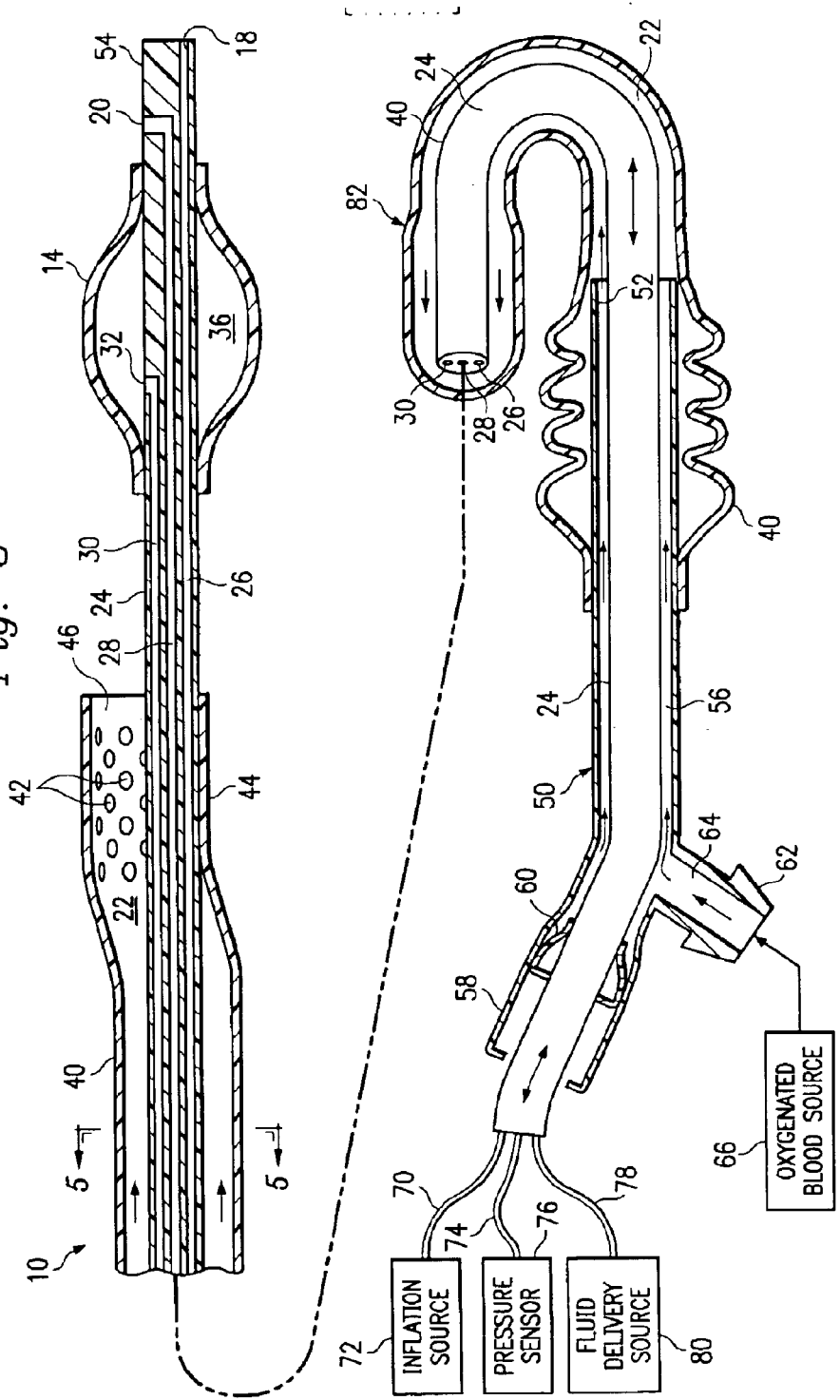
FIG. 3 is a longitudinal cross section of the catheter of FIG. 1 illustrating the large lumen in the expanded state when fluid flows therethrough into the body vessel.
Figure 4:
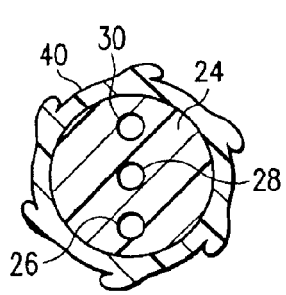
FIG. 4 is a transverse cross-section of the catheter taken along line 4—4 in FIG. 2 with the large lumen in the collapsed state.
Figure 5:
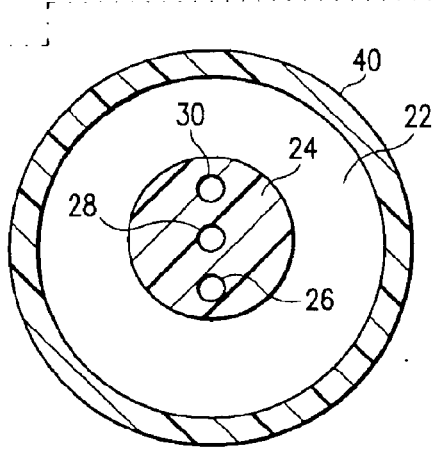
FIG. 5 is a transverse cross-section of the catheter taken along line 5—5 in FIG.3 with the large lumen in the expanded state.

Referring now to FIG. 2 and FIG. 3, there is shown a longitudinal cross section of catheter 10 according to the preferred embodiment. Sleeve member 40 is illustrated in the collapsed state in FIG. 2, and in the expanded state in FIG. 3. A transverse cross-section of catheter 10 having the sleeve member 40 in the collapsed state taken along line 4—4 in FIG. 2 is shown in FIG. 4. A transverse cross-section of catheter 10 having the sleeve member 40 in the expanded state taken along line 5—5 in FIG. 3 is shown in FIG. 5. It is noted again that the catheter 10 is ideally suited as an aortic balloon catheter, however, the catheter 10 has other intended uses as well, such as a ureter catheter, and limitation for use as an aortic balloon catheter as described with reference to FIG. 1 is not to be inferred.

Catheter 10 is seen to have the main catheter body 24 which may be comprised of a conventional material such as polyvinylchloride (PVC), polyurethane, and polyethylene, although limitation to these materials is not to be inferred as catheter body 24 can be comprised of elastomeric materials as well, such as silicone. Extending within catheter body 24 is a plurality of lumens including a first lumen 26 extending to distal port 18, a second lumen 28 extending to distal port 20, and third lumen 30 extending to a balloon inflation port 32 within balloon member 14. Also shown is balloon member 14 being sealingly disposed about the distal end of the catheter body 24 to form a cavity 36 therewithin. When used as an aortic perfusion catheter, aortic root pressure is sensed via lumen 28 and port 20 above the aortic valve 16 to determine if the balloon member 14 is properly occluding the ascending aorta 11. Then, cardioplegia is delivered to the aorta proximate the aortic valve 16 via the lumen 26 and port 18 while sensing pressure at the aortic root to maintain a pressure of about 50–100 mm Hg.

The integral expandable/collapsible lumen 22 is formed by the thin-walled flexible lumen member 40 secured about and carried by the main catheter body 24. Lumen member 40 is preferably secured only at the distal end thereof at 41, but may alternatively be secured along a line to the outer surface of the main catheter body 24, either intermittently or continuously along catheter body 24 if desired. Securing lumen member 40 to catheter body 24 ensures that the distal end of member 40 is carried with main catheter body 24 of catheter 10 during insertion.

Lumen member 40 preferably has a plurality of circumferentially extending openings 42 disposed at the member distal end 44, whereby lumen 22 terminates at a distal lumen opening at 46. Lumen opening 46 and sidewall openings 42 facilitate infusing fluid out the distal end of the large lumen 22 when expanded by the fluid pressure. Advantageously, lumen member 40 has a very thin wall thickness to maintain a low profile when collapsed about catheter body 24, as shown in FIG. 2 and FIG. 4. The collapsed lumen member 40 is folded and wrapped about the catheter body 24 and heated during manufacturing to keep the member close to catheter body 24, as shown in FIG. 4, until unfolded when inflated. Member 40 has a wall thickness preferably in the range of 0.002 inches, and preferably less than 0.01 inches, and is preferably comprised of a strong and resilient material such as polyethylene. Thus, the relative thickness of member 40 is not drawn to scale in FIG. 2 and FIG. 3. However, other dimensions and other conventional materials can be utilized as well, and limitation to polyethylene is not to be inferred. For instance, PVC, and polyurethane are suitable as well. The material chosen for lumen member 40 could be the same as the catheter body 24 to facilitate a secure attachment thereto using conventional mechanical, chemical or thermal bonding techniques.

In the preferred embodiment, the inner diameter of lumen 22 in the expanded position, as shown in FIG. 3 and FIG. 5, is substantially larger than the outer diameter of the main catheter body 24, such as a 4 to 1 ratio. For example, the inner diameter of expanded lumen 22 may be about 10.7 mm (32 fr.), and the outer diameter of main catheter body 24 may be about 2.7 mm (8 fr.), although limitation to these dimensions is not to be inferred. This expandable lumen 22 is ideal for delivering a fluid, such as oxygenated blood, at a large fluid rate, whereby the smaller lumens 26, 28 and 30 are rather small and suited for their intended use, such as previously discussed. The main catheter body 24 is comprised of a suitable material such that it will not kink or buckle during insertion into the intended body vessel, such as the aorta or urethra. If desired, one of the lumens, such as lumen 26, can be provided with a malleable guide wire to selectively provide rigidity to the catheter body 24 and aid insertion of catheter 10 into the intended body vessel.

Cessation of fluid flow from the pump (not shown) through the lumen 22 will cause the lumen member 40 to collapse about the catheter body 24. Removal of catheter 10 from the body vessel, generally after fluid flow through lumen 22 has ceased, will further constrict lumen member 40 to cause any remaining fluid in lumen 22 to be dispensed out the distal opening 46 of the lumen 22. The lumen member 40 having a very flexible and thin wall will collapse about catheter body 24 as forces from the body vessel compress the lumen member 40 into its collapsed position, thus facilitating the easy removal of catheter 10 from the body vessel. The reduced catheter diameter during withdrawal further reduces trauma to the body vessel, which is a further technical advantage.

Still referring to FIG. 2 and FIG. 3, the proximal end of catheter 10 is seen to have versatile features that have additional technical advantages. Each patient has different physical attributes and dimensions, and thus, the catheter can be adapted to have a sufficient length for use within each particular patient. The proximal end of catheter 10 is seen to have a substantially rigid tubular body member generally shown at 50. The proximal end of the thin wall lumen member 40 is seen to be disposed about and sealingly attached about the circumference of the body member 50 distal end shown at 52. Notably, the proximal end of the lumen member 40 is seen to be bunched together in an accordion or serpentine like arrangement. This allows the length of the lumen member 40 defined distal of the distal end 52 to be selectively adjusted along with the length of catheter body 24 slidably extending body member 50, thereby allowing the physician to selectively adjust the length of the catheter from body member distal end 52 to the catheter distal end 54. As indicated by the arrows, the main catheter body 24 is seen to be longitudinally slidably adjustable within a flow passageway 56 extending within body 50. Main catheter body 24 can be selectively adjusted by the physician such that it can be extended or retracted through body member 50 and proximal end 58. To provide a sealed, fluid tight, lumen 56, the proximal end 58 of body member 50 has positioned therein a hemostasis valve 60 sealingly-disposed about the main catheter body 24. Valve 60 is sealingly engaged against the inner wall of passageway 56 to prevent oxygenated blood 66 from back flowing through proximal end 58, and to provide friction holding catheter body 24 in place at the selected position. The main catheter body 24 is longitudinally and slidably adjustable through valve 60 by the physician.

A flanged connector 62 is seen to form a Y connection in combination with proximal end 58 and has a passageway 64 extending therethrough in fluid communication with passageway 56. An oxygenated blood source 66 is fluidly coupled to member 62 and provides oxygenated blood to the catheter 10 via the passageway 64, lumen 56, and ultimately to the expandable/collapsible passageway 22 for delivery to the artery via the opening 46 and openings 42. The proximal end of catheter 10 is seen to have extending therefrom three separate passageways, namely, a passage 70 in fluid communication with lumen 30 and coupled to an inflation source 72, a passageway 74 in fluid communication with lumen 28 and coupled to a pressure sensor device 76, and a passageway 78 in fluid communication with lumen 26 and coupled to a fluid delivery source 80. Each passageway connects to a respective connector, as shown in FIG. 1.

The outer diameter of main catheter body 24 is significantly smaller than the outer diameter of passageway 56 extending through body member 50. This creates a sufficient passageway 56 about main catheter body 24 for oxygenated blood to be communicated therethrough at a sufficient rate and pressure to perfuse the human body as shown in FIG. 1. It is noted that the outer diameter of passageway 56 is less than the diameter of passageway 22 formed by the fully inflated lumen member 40, and thus, the fluid pressure will be higher through passageway than the fluid pressure within passageway 22 during use. However, the short catheter portion that the blood is at a higher pressure is relatively short in relation to the overall length of the catheter 10. Thus, the required pressure for the oxygenated blood source 66 is suitable for delivery of oxygenated blood to an artery of the body, such as the aorta illustrated in FIG. 1. As shown in FIG. 3, the diameter of the lumen member 40 between proximate body member 50 and a transition 82 is reduced with respect to the lumen member 40 distal of transition 82 as this portion and the body member distal end 52 typically are positioned in the smaller access artery. The body member 50 has sufficient strength to facilitate insertion into a smaller access artery.

Figure 6:
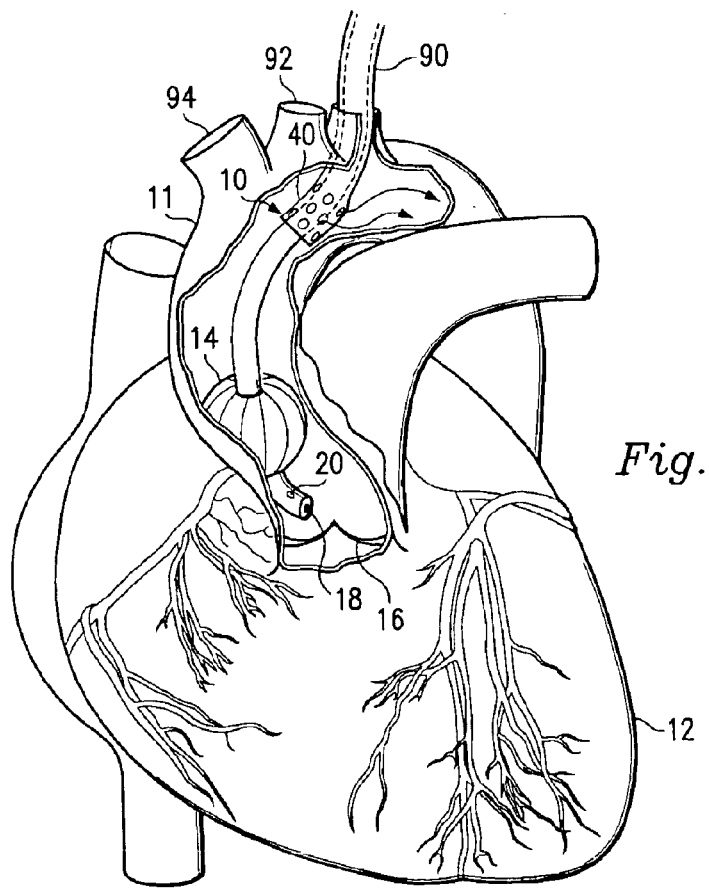
FIG. 6 is a view of the catheter inserted into the aorta via the left subclavian artery.

Referring now to FIG. 6, there is shown an alternative method of the use whereby the catheter 10 is inserted into the ascending aorta via the left subclavian artery shown at 90. Like the femoral artery, the left subclavian artery can also be used as an access vessel for positioning the catheter 10 within the ascending aorta, as shown. The left subclavian artery, like the femoral artery, has a diameter less than the larger aortic artery and thus limits the overall diameter of the catheter that can be inserted therethrough. The catheter is ideal for insertion through small arteries for ultimate positioning within a larger artery, such as for the purpose of delivering fluids into the large artery at suitable flow rates while minimizing trauma to the arteries by the catheter.

It is intended that other arteries are suitable as access sites for the catheter as well, such as the left carotid artery 92 and the right carotid artery 94 as shown in FIG. 6. The desired insertion artery is left to the choice of the surgeon and will depend upon many criteria and will vary from patient.

FIGS. 7–11 describe various examples and other embodiments. For brevity and clarity, a description of those parts which are identical or similar to those described in connection with embodiments illustrated in FIGS. 1 through 6 will not be repeated. Reference should be made to the foregoing paragraphs with the following description to arrive at a complete understanding of these embodiments. It is understood that features of various examples and embodiments may be interchanged, combined or otherwise reconfigured.

Referring to FIG. 11a, which is an isometric side view of another embodiment designated generally as a catheter 1100 which includes an elongated collapsible lumen 1102, a catheter body 1108, and a connection 1110.

The collapsible lumen 1102 preferably has a diameter sufficient to infuse oxygenated blood into an aorta at a suitable flow rate and flow pressure to perfuse a human body. Advantageously, collapsible lumen 1102 has a very thin wall thickness to maintain a low profile when collapsed, preferably in the range of 0.003 inches or less. The collapsible lumen 1102 is preferably comprised of a strong and resilient material such as polyurethane. However, other dimensions and other conventional materials can be utilized as well, and limitation to polyurethane is not to be inferred. For instance, PVC, and polyethylene are suitable as well. In one embodiment, the material chosen for collapsible lumen 1102 could be the same as the catheter body 1108 to facilitate a secure attachment thereto using conventional mechanical, chemical or thermal bonding techniques.

Figure 11B:
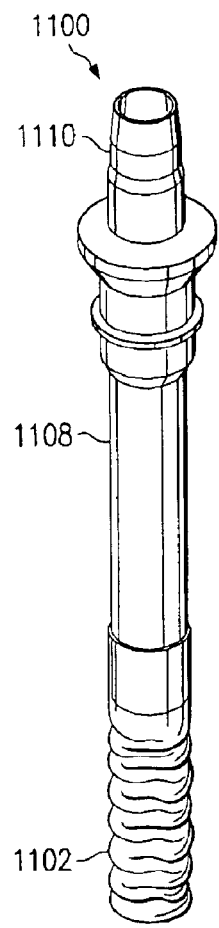
FIG. 11b is an isometric side view of one embodiment showing an expanded lumen in a partially expanded position.
Figure 11C:
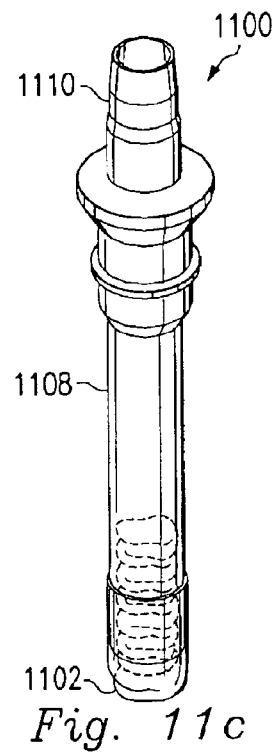
FIG. 11c is an isometric side view of one embodiment showing an expanded lumen folded back into the body of a catheter.
Figure 11D:
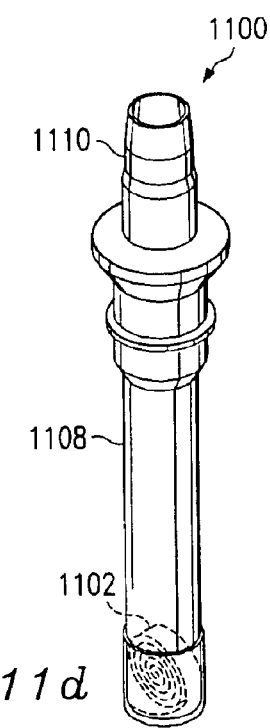
FIG. 11d is an isometric side view of one embodiment showing a lumen rolled into the body of a catheter.

In FIG. 11a the collapsible lumen 1102 is shown in a fully extended condition. In FIG. 11b, the collapsible lumen 1102 is shown partially extended to illustrate the extremely pliable and flexible nature of the collapsible lumen 1102. Because the collapsible lumen 1102 is so pliable, it can be "collapsed" or fitted inside of catheter body 1108 as shown in FIG. 11c. FIGS. 11c and 11d illustrate different embodiments of the collapsible lumen 1102 in a collapsed condition. The collapsible lumen 1102 can also be rolled up inside the catheter body as shown in FIG. 11d. Other collapsed conditions are possible, and a limitation to these conditions should not be inferred. In operation, the catheter 1100 can be inserted into a artery in the usual manner. Once catheter connection 1110 is connected to a heart-lung machine and fluids start flowing, the fluid pressure will cause the collapsible lumen 1102 to expand longitudinally, as illustrated in FIG. 11a.

Figure 11E:
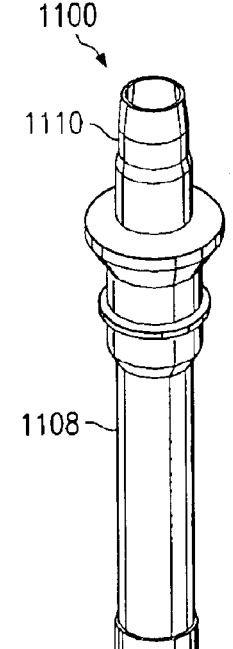
FIG. 11e is an isometric side view of one embodiment showing an expanded lumen having a large diameter.

In another embodiment, illustrated in FIG. 11e, a collapsible lumen 1112 has a larger cross-sectional diameter than the catheter body 1108. A larger diameter would allow the collapsible lumen 1112 to conform to the interior of the artery or vessel without causing trauma to the inside of the artery during insertion. The larger diameter would also allow for a reduced flow velocity causing less trauma to the interior of the vessel or artery.

In another embodiment, the collapsible lumen could have a smaller cross-sectional diameter or a reduced cross-sectional diameter at the distal end of the member. Referring to FIG. 7a, which illustrates an isometric view of another embodiment designated generally as catheter 700 which includes an elongated collapsible lumen 702, a catheter body 708, and a connection 710. The distal end of collapsible lumen 702 terminates at nozzle 718. The diameter of nozzle 718 tapers to a reduced diameter opening 720 or, alternatively, no opening. In either case, there are a plurality of circumferentially extending side openings 716 disposed longitudinally along nozzle 718. The plurality of side openings create a diffused velocity flow versus the high velocity flow or "jet" flow of a single opening in a standard cannula. The diffused velocity flow reduces the possibility of dislodging micro-emboli from the aorta wall and other trauma to the inside of the aorta.

In embodiments incorporating the end opening 720, the tapered shape of nozzle 718 causes a reduction in the cross-sectional area of the lumen, which increases the pressure forcing fluid out side openings 716. In another embodiment illustrated in FIG. 7b, the side openings 716 can be on the straight section of a collapsible lumen 724. In this embodiment the distal end 726 has a reduced end opening or no opening at all. If the side openings 716 are used in this embodiment without the end opening 720, the flow out of the side openings will create more turbulence in the fluid flow-which is less desirable. On the other hand, if side openings are used in this embodiment with a end opening that has not been tapered, most of the fluid flow will go through the end opening and little or no flow will be through the side openings 716.

Figure 9E:
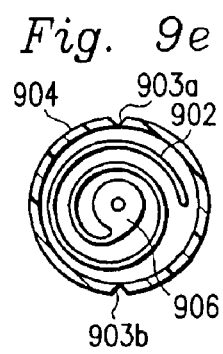

The openings 716 shown in FIGS. 7a–7d are illustrated as circular openings. However, other shape openings may also be used, for instance straight or arrow-shaped slits would also be effective at reducing the velocity of the flow. FIG. 9d illustrates another embodiment, discussed later, where the openings 930 are slits. The use of slits creates even a softer flow than circular holes, while keeping the flow directed forward.

The collapsible lumen member can be attached to a variety of cannulae and catheter bodies. Turning back to FIG. 7a, the proximal end of collapsible lumen 702 is joined to a catheter body 708 at point 714. The collapsible lumen 702 is preferably disposed about and sealingly attached about the circumference of the catheter body 708.

The main body section 707 is used to clamp the cannula. The larger diameter of the main body section 707 reduces the pressure drop across the cannula. At the proximal end of the main body section 707 is a connection 710. The connection 710 is attached to the arterial line of a an extracorporeal bypass machine.

The reinforced section 704 has a smaller diameter than the main body section 707. The smaller diameter allows for a smaller insertion site. The reinforced section 704 is reinforced by a semi-rigid support member comprising a helical spring or coil which keeps reinforced section 704 from kinking during insertion and use. The spring is made from wire which has a relatively small cross-sectional diameter and helically extends within the body of reinforced section 704. The wire is preferably integrated into the body of reinforced section 704 during a manufacturing extrusion process forming the catheter body 708. A transition section 706 couples the reinforced section 704 to a main body section 707. Both the reinforced section 704 and main body section 707 are cylindrical in shape. Main body section 707 has a larger diameter and wall thickness than reinforced section 704. Transition section 706 is tapered which allows for a smooth transition between the main body section 707 and reinforced section 704.

The main body section 707 is used to clamp the cannula. The larger diameter of the main body section 707 reduces the pressure drop across the cannula. At the proximal end of the main body section 707 is a connection 710. The connection 710 is attached to the arterial line of a an extracorporeal bypass machine, The catheter 700 may be used for different medical procedures by varying the length of the collapsible lumen 702. For instance, if the collapsible lumen member is relatively short (approximately 1 inch) as illustrated by a collapsible lumen 722 in FIG. 7c, the catheter may be used to perfuse blood in the ascending aorta or directly inserted in the distal aortic arch to perfuse blood in the descending aorta. Alternatively, if the collapsible lumen member is relatively long as illustrated in FIGS. 7a and 7b, the catheter may be inserted from the femoral artery. Side openings 716 may be located only in the region of nozzle 718 as illustrated in FIG. 7a for perfusion only in the descending aorta. Alternatively, as illustrated in FIG. 7b, side openings may be located all along the periphery of a collapsible lumen 724 for perfusion in throughout the aortic arch.

Referring to FIG. 7d, which illustrates another embodiment. In this embodiment, catheter 750 is similar to the catheter illustrated in FIG. 7c, except that it is coupled to a balloon member 752. In FIG. 7d, the balloon member 752 is in an expanded condition. The balloon member 752 is used to occlude an artery, and is positioned longitudinally between a body portion 753 and a collapsible lumen 722. Catheter 750 is used to perfuse, and balloon member 752 occludes the aorta above an aortic valve 16, as illustrated in FIG. 10d. Balloon member 752 is inflated by a separate tube (not shown) running down the interior wall of the catheter body 753.

Referring back to FIG. 7a, the collapsible lumen 702 may be expanded due to flow pressure. The surgeon also has an option to expand the collapsible lumen 702 before the connection 710 is attached to a heart-lung machine by using a dilator 730. The dilator 730 may be used to expand, insert and position catheter 700 in the aorta. The dilator 730 should have an outside diameter that easily fits within the inner diameter of collapsible lumen 702 and catheter body 708. The dilator 730 is preferably comprised of a flexible material, such as polyethylene or silicone, to curve around the aortic arch. However, a flexible material may be difficult to insert, therefore to aid in the insertion the proximal end of the dilator shall be of a more rigid material or a larger wall thickness.

In this embodiment, catheter 700 is inserted into the body using standard insertion procedures and techniques. After the catheter 700 is inserted, a collapsible lumen 702 would be pushed out by the dilator 730 as illustrated in FIG. 7a. The collapsible lumen 702 can also be inflated after connection 710 was connected to an extracorporeal circuit (not shown). The pressure from a roller pump (not shown) could then force the collapsible lumen 702 to expand to its full extended position within the body vessel.

Figure 10B:
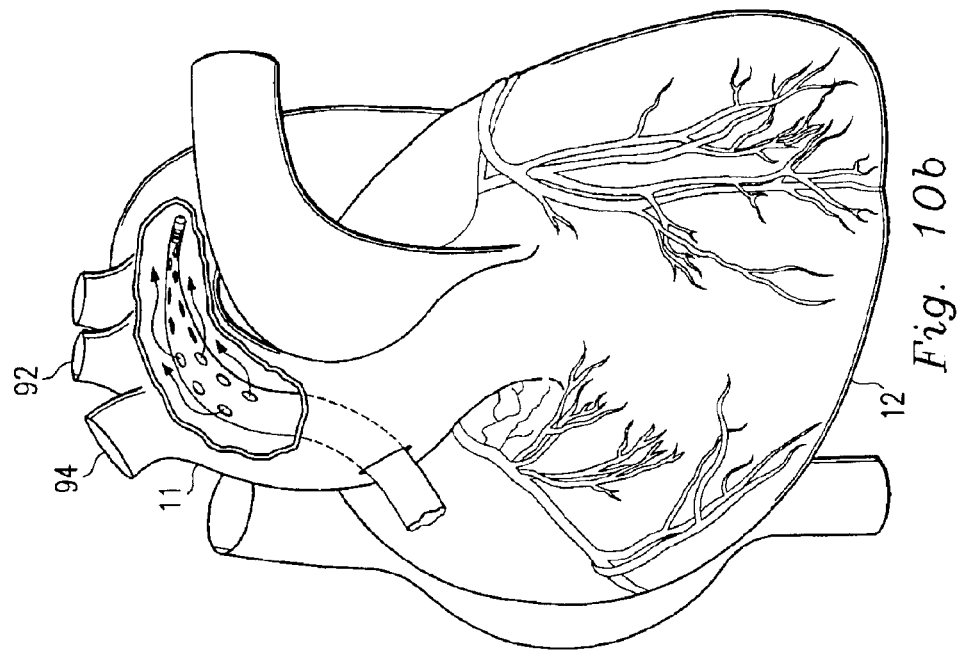
FIG. 10b is a view of the embodiment shown in FIG. 7b inserted into the aortic arch and perfusing the descending aorta.
Figure 10A:
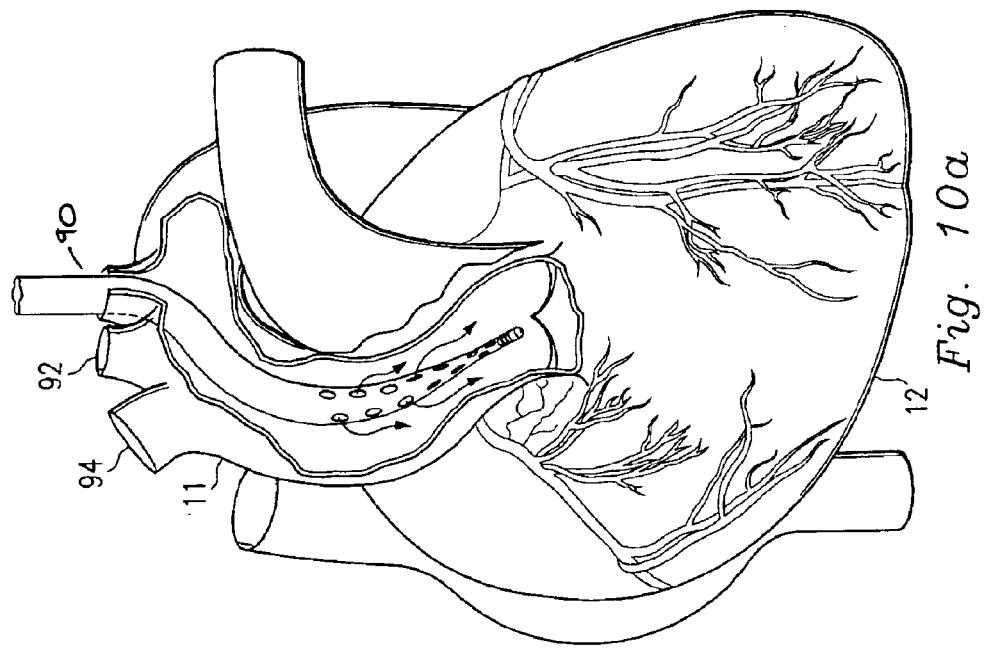
FIG. 10a is a view of one embodiment inserted into the aorta via the left subclavian artery.

Referring now to FIG. 10a, there is shown an alternative method whereby the catheter 700 is inserted into the ascending aorta via the left subclavian artery shown at 90. Like the femoral artery, the left subclavian artery can also be used as an access vessel for positioning the catheter 700 within the ascending aorta, as shown. The left subclavian artery, like the femoral artery, has a diameter less than the larger aortic artery and thus limits the overall diameter of the catheter that can be inserted therethrough. The catheter is ideal for insertion through small arteries for ultimate positioning within a larger artery, such as for the purpose of delivering fluids into the large artery at suitable flow rates while minimizing trauma to the arteries by the catheter.

Referring to FIG. 10b, there is shown an alternative method whereby the catheter 700 is inserted into the aortic arch for perfusing the descending aorta. Like the femoral artery, the aortic arch can also be used as an access vessel for positioning the catheter 700 within the descending aorta, as shown.

Referring to FIG. 10c, there is shown another alternative method of use wherein the catheter 700 is directly perfusing the aortic arch as shown in FIG. 10c.

Referring to FIG. 10d, there is shown an alternative method whereby the catheter 750 is inserted into the aortic arch for perfusing the descending aorta. Like the femoral artery, the aortic arch can also be used as an access vessel for positioning the catheter 750 within the descending aorta, as shown. The balloon member 752 is expanded which occludes the aorta above the aortic valve 16 (not shown in FIG. 10d).

Figure 8:
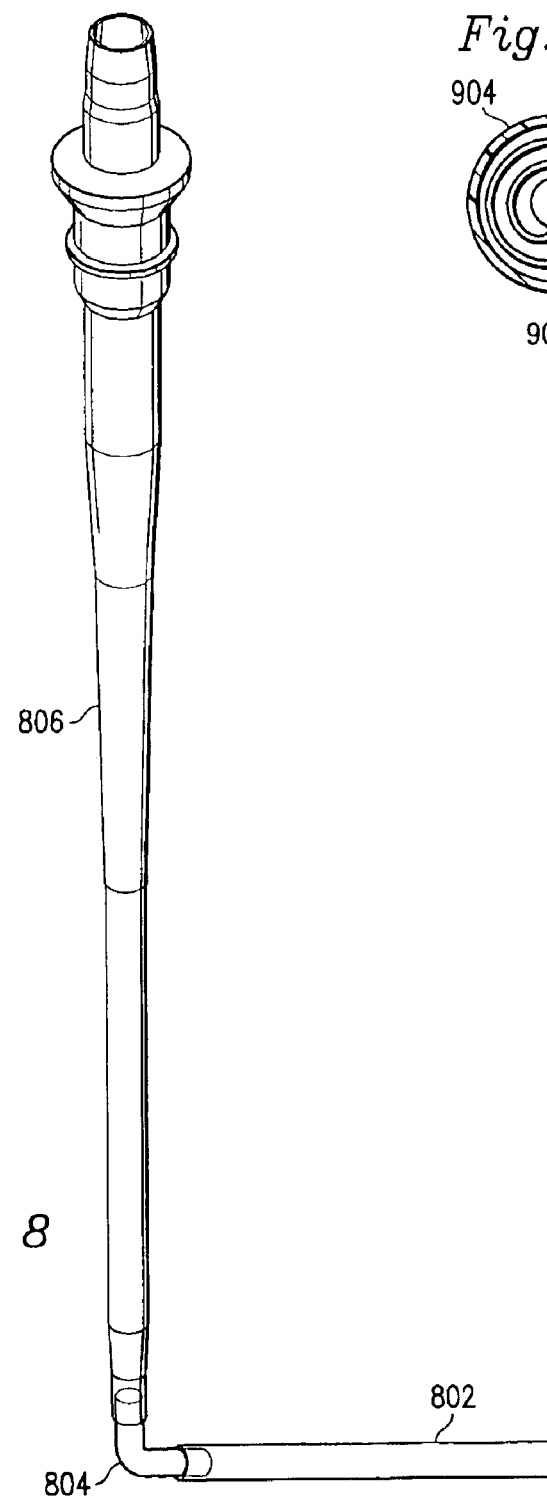
FIG. 8 is an isometric side view of another embodiment.

Referring to FIG. 8, which shows another embodiment of a collapsible lumen 802 in an expanded condition and attached to a curved tip 804 of a vascular cannulae 806. The collapsible lumen 802 could also be directly attached to the vascular cannulae 806. The collapsible lumen 802 may be rolled up or collapsed into the body of the vascular cannulae 806, similar to the collapsible lumen 1102 of FIGS. 11c and 11d.

Figures 9A, 9C:
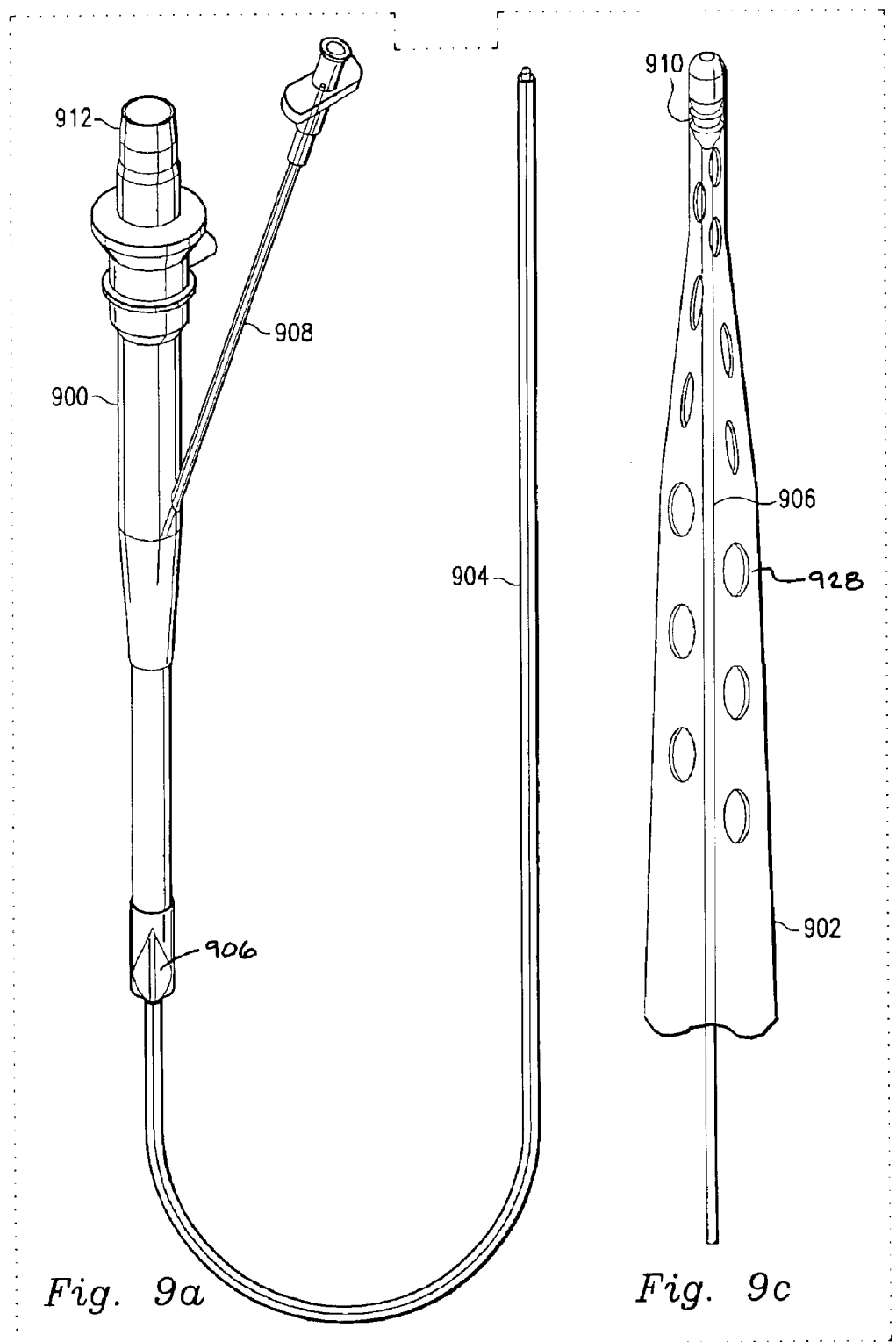
FIG. 9a is an isometric drawing of another embodiment showing the flexible lumen in a collapsed position inside a cover.
FIG. 9c is a detailed isometric drawing of a diffused nozzle used in some embodiments.
Figures 9B, 9D:
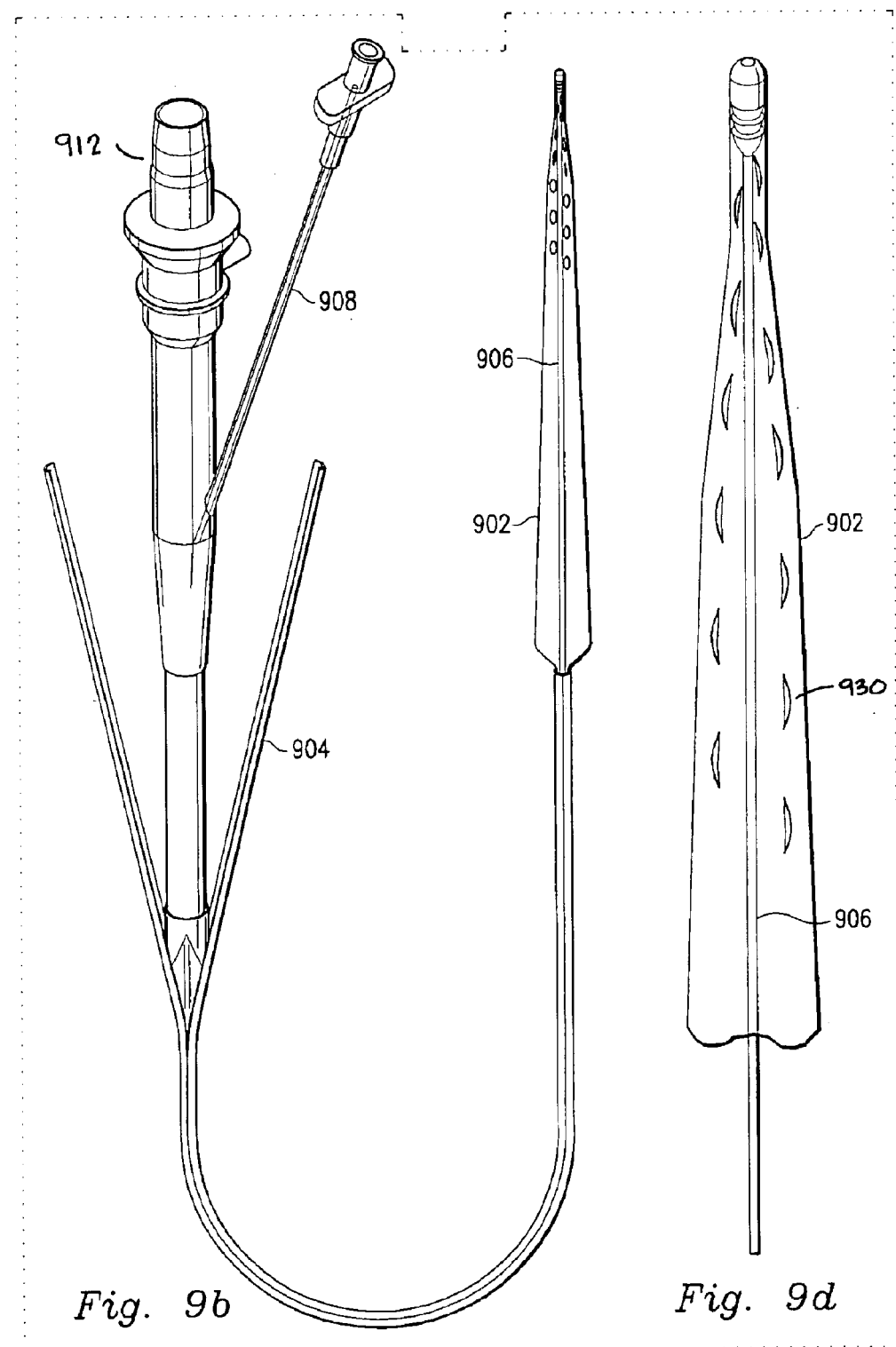
FIG. 9b is an isometric drawing of the embodiment illustrated in FIG. 9a showing a partially removed cover.
FIG. 9d is a detailed isometric drawing of another diffused nozzle used in some embodiments.

In another embodiment, illustrated in FIG. 9a, a catheter 900 comprises a cover 904 and a tube member 906 to assist in the positioning of the catheter 900. The catheter 900 is similar to the catheter 700, except that a collapsible lumen 902 (not shown in FIG. 9a) is folded or collapsed inside the cover 904.

FIG. 9e is a transverse cross-section view through the cover 904, the tube member 906, and the collapsible lumen 902. At the center is the tube member 906. Surrounding the tube member 906 is the collapsible lumen 902 which in a collapsed state and is folded around tube member 906. The cover 904 encapsulates and surrounds the collapsible lumen 902. The cover 904 can be made from PVC, polyurethane or another suitable material. As shown in FIG. 9e, notches 903a and 903b are shown which run longitudinally along the periphery of the cover 904. The notches 903a and 903b weakens the radial strength of the cover 904 to allow for easy removal of the cover 904.

The tube member 906 may be manufactured by any wide variety of stainless or other medical grade materials. If a guide wire is used, the tube member 906 may be hollow which allows it to slide over a guide wire. The interior diameter of tube member 906 is sufficient to allow the tube member 906 to slide over the guide wire. If a guide wire is not used, tube member 906 may be either solid or hollow. At the distal end, the tube member 906 is coupled to a rounded end member 910 as illustrated in FIG. 9c. FIG. 9c is a detail view of the distal end of the collapsible lumen 902, having circular openings 928. FIG. 9d is an alternative embodiment wherein the openings 930 are longitudinal slits. The use of end member 910 reduces the chances of a creating a "whipping" action within the vessel as the tube is snaked through the vessel. The end member 910 also reduces the chances of scraping the interior of the artery. Furthermore, it easily identifiable in TEE screens. The end member 910 may be made from stainless steel, nylon or any number of medical grade materials. The end member 910 is sealantly attached to the collapsible lumen 902. The tube member 906 runs from the distal end of collapsible lumen 902, through the body of catheter 900, through side port 908 (FIG. 9a).

In operation, catheter 900 is inserted into the femoral artery or another suitable insertion point. At the surgeon's option, a guide wire (not shown) may be used to assist in positioning catheter 900. If a guide wire is used, tube member 906 may be slid over the guide wire until the catheter is in position. Once the catheter is in position, the guide wire may be removed by pulling it through side port 908.

The surgeon may also choose to position catheter 900 without the aid of a guide wire. Compared to the collapsible lumen 902, the cover 904 is relatively rigid and allows for the insertion and accurate positioning of the collapsible lumen 902 within the artery. Because collapsible lumen 902 is in a collapsed position inside of cover 904, the collapsible lumen 902 has an extremely low profile which significantly reduces the chances of trauma or dislodging plaque. Once the collapsible lumen 902 is in position, cover 904 may be removed by pulling the sheath longitudinally toward the catheter body 900, as illustrated in FIG 9b. Cover 904 may then be discarded and the collapsible lumen 902 is inflated by fluid pressure created by a roller up (not shown) once connecting member 912 is connected to an extracorporeal circuit (not shown).

Cessation of fluid flow from the pump in the extracorporeal circuit through the collapsible lumen will cause the collapsible lumen to collapse. Removal of the catheter from the body vessel can take place generally after fluid flow through the collapsible lumen has ceased. The removal will further constrict the collapsible lumen and cause any remaining fluid in the collapsible lumen to be dispensed out the openings at the distal end, thus facilitating easy removal from the body vessel. The reduced catheter diameter during withdrawal further reduces trauma to the body vessel, which is a further technical advantage.

The catheter is also ideal for insertion through small arteries for ultimate positioning within a larger artery, such as for the purpose of delivering fluids into the large artery at suitable flow rates while minimizing trauma to the arteries by the catheter. It is intended that other arteries are suitable as access sites as well, such as the left carotid artery 92 and the right carotid artery 94. The desired insertion artery is left to the choice of the surgeon and will depend upon many criteria and will vary from patient to patient.

In summary, the present invention achieves technical advantages as a catheter which has the functional characteristics of a catheter having a predetermined outer diameter, but which during insertion and withdrawal has a smaller effective overall diameter. The present invention achieves advantages of a reduced-diameter single catheter which is suitable for insertion into smaller access arteries to reduce trauma to the arteries or blood vessels during insertion and withdrawal, while providing significant fluid flow therethrough to and toward the distal end of the catheter.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

What is claimed:

1. A catheter comprising:
   a catheter body, wherein the catheter body is elongated and hollow, the catheter body having a distal and a proximal end, wherein the catheter body comprises a rigid member with a proximal and a distal end, and;
   a hollow support member coupled to the catheter body having a distal and proximal end, wherein the proximal end of the support member is coupled to the distal end of the catheter body and wherein the proximal end of the support member is coupled to the distal end of the rigid member; and
   a collapsible lumen having a distal and proximal end, wherein the proximal end of the lumen is coupled to the distal end of the support member, wherein the lumen is flexible relative to the catheter body and has a plurality of openings to allow fluid to flow through the lumen such that the velocity of the fluid flow through the lumen is minimized.

2. The catheter of claim 1 wherein the lumen has a diameter which decreases from the proximal end to the distal end.

3. The catheter of claim 1 further comprising a dilator with an outside diameter smaller than the inside diameter of the lumen such that the dilator can be slidably positioned into the lumen to longitudinally support the lumen during insertion.

4. The catheter of claim 1, wherein the human is adaptable to be collapsed.

5. The catheter of claim 1, further comprising an opening positioned on the distal end of the collapsible lumen.

6. The catheter of claim 1, further comprising a nozzle on the distal end of the collapsible lumen, wherein the nozzle has a plurality of openings disposed around a periphery of the collapsible lumen.

7. The catheter of claim 6, wherein the opening is positioned on the distal end of the nozzle.

8. The catheter of claim 6, wherein the plurality of openings are proximate to the distal end of the collapsible lumen.

9. The catheter of claim 6, wherein the plurality of openings are disposed around the periphery of the collapsible lumen from the distal end of the collapsible lumen to the proximal end of the collapsible lumen.

10. The catheter of claim 6, wherein the nozzle is tapered.

11. The catheter of claim 6, wherein the openings comprise slits.

12. The catheter of claim 11, wherein the slits comprise V-shaped slits.

13. The catheter of claim 1, wherein the support member comprises a tubular member and a coil, and the coil is disposed within the tubular member.

14. The catheter of claim 1, further comprising an inflatable balloon member disposed about the catheter body.

15. The catheter of claim 14, further comprising a tube within the catheter body and coupled to the inflatable balloon member for coupling the inflatable balloon member to a pressure source.

* * * * *

UNITED STATES PATENT AND TRADEMARK OFFICE
CERTIFICATE OF CORRECTION

PATENT NO.    : 6,951,555 B1
DATED         : October 4, 2005
INVENTOR(S)   : Suresh et al.

It is certified that error appears in the above-identified patent and that said Letters Patent is hereby corrected as shown below:

Column 12,
Line 1, delete "human" and substitute -- lumen --.

Signed and Sealed this

Tenth Day of January, 2006

JON W. DUDAS
*Director of the United States Patent and Trademark Office*